(12) United States Patent
Melchiorri et al.

(10) Patent No.: US 12,371,645 B2
(45) Date of Patent: Jul. 29, 2025

(54) SELECTIVE MEMBRANE-DRIVEN GAS TRANSFER DEVICE AND METHODS

(71) Applicant: ARBOREA LTD, Surrey (GB)

(72) Inventors: Julian Paul Melchiorri, Surrey (GB); Tristan Dell, Melksham (GB)

(73) Assignee: ARBOREA LTD, Surrey (GB)

( * ) Notice: Subject to any disclaimer, the term of this patent is extended or adjusted under 35 U.S.C. 154(b) by 0 days.

(21) Appl. No.: 18/905,320

(22) Filed: Oct. 3, 2024

(65) Prior Publication Data

US 2025/0027016 A1  Jan. 23, 2025

Related U.S. Application Data

(62) Division of application No. 15/780,774, filed as application No. PCT/GB2016/053786 on Dec. 1, 2016, now abandoned.

(30) Foreign Application Priority Data

Dec. 1, 2015 (GB) .................................. 1521136

(51) Int. Cl.
| | |
|---|---|
| *C12M 1/00* | (2006.01) |
| *B01D 53/22* | (2006.01) |
| *B01D 69/10* | (2006.01) |
| *B01D 71/70* | (2006.01) |
| *C12M 1/02* | (2006.01) |
| *C12M 1/04* | (2006.01) |
| *C12M 1/12* | (2006.01) |

(Continued)

(52) U.S. Cl.
CPC ............. *C12M 21/02* (2013.01); *B01D 53/22* (2013.01); *B01D 53/228* (2013.01); *B01D 69/10* (2013.01); *B01D 71/70* (2013.01); *B01D 71/701* (2022.08); *C12M 1/002* (2013.01); *C12M 23/06* (2013.01); *C12M 23/20* (2013.01); *C12M 23/22* (2013.01); *C12M 23/24* (2013.01); *C12M 25/00* (2013.01); *C12M 25/02* (2013.01); *C12M 27/00* (2013.01); *C12M 31/00* (2013.01); *C12M 33/00* (2013.01); *C12M 41/12* (2013.01); *C12M 41/48* (2013.01); *B01D 2325/38* (2013.01)

(58) Field of Classification Search
None
See application file for complete search history.

(56) References Cited

U.S. PATENT DOCUMENTS

| | | | |
|---|---|---|---|
| 3,510,387 A | 5/1970 | Robb | |
| 3,873,423 A | 3/1975 | Munder et al. | |

(Continued)

FOREIGN PATENT DOCUMENTS

| | | |
|---|---|---|
| CN | 204335434 U | 5/2015 |
| DE | 102012013587 A1 | 1/2014 |

(Continued)

OTHER PUBLICATIONS

Carvalho et al., "Microalgal Reactors: A Review of Enclosed System Designs and Performances." Biotechnology Progress 22(6): 1490-1506 (2006).

(Continued)

*Primary Examiner* — Duane Smith
(74) *Attorney, Agent, or Firm* — Nixon Peabody LLP; David S. Resnick; Nicole D. Kling

(57) ABSTRACT

Described herein are methods and devices for selective membrane-driven gas transfer.

16 Claims, 13 Drawing Sheets

(51) Int. Cl.
*C12M 1/26* (2006.01)
*C12M 1/34* (2006.01)
*C12M 1/36* (2006.01)

(56) References Cited

U.S. PATENT DOCUMENTS

| | | | |
|---|---|---|---|
| 3,941,662 | A | 3/1976 | Munder et al. |
| 4,661,455 | A | 4/1987 | Hubbard |
| 4,666,668 | A * | 5/1987 | Lidorenko ............ B01D 71/70 428/447 |
| 5,686,304 | A | 11/1997 | Codner |
| 6,306,491 | B1 * | 10/2001 | Kram .................... B01D 69/00 428/305.5 |
| 6,900,055 | B1 | 5/2005 | Fuller et al. |
| 7,560,274 | B1 | 7/2009 | Fuller et al. |
| 7,964,392 | B2 | 6/2011 | Hatano et al. |
| 8,365,462 | B2 | 2/2013 | Licamele et al. |
| 8,409,845 | B2 | 4/2013 | Trent et al. |
| 9,469,832 | B2 | 10/2016 | Mena Mas |
| 2006/0199260 | A1 | 9/2006 | Zhang et al. |
| 2008/0044850 | A1 | 2/2008 | Taylor et al. |
| 2009/0209035 | A1 | 8/2009 | Watanabe |
| 2009/0305389 | A1 | 12/2009 | Willson et al. |
| 2010/0162621 | A1 | 7/2010 | Seebo |
| 2010/0190236 | A1 | 7/2010 | Delobel |
| 2010/0216203 | A1 | 8/2010 | Trent et al. |
| 2010/0261918 | A1 | 10/2010 | Chianelli et al. |
| 2011/0104890 | A1 | 5/2011 | Kumamoto et al. |
| 2011/0151547 | A1 | 6/2011 | Bloch et al. |
| 2011/0312084 | A1 | 12/2011 | Delprat et al. |
| 2011/0318804 | A1 | 12/2011 | Posten et al. |
| 2011/0318819 | A1 | 12/2011 | Legendre et al. |
| 2012/0040453 | A1 | 2/2012 | Zal |
| 2012/0107792 | A1 | 5/2012 | Babbitt et al. |
| 2012/0135513 | A1 | 5/2012 | Muller-Rees et al. |
| 2012/0202290 | A1 | 8/2012 | Mueller-Rees et al. |
| 2012/0220020 | A1 | 8/2012 | Mueller-Rees et al. |
| 2012/0270304 | A1 | 10/2012 | Johnson et al. |
| 2012/0309090 | A1 | 12/2012 | Aikens et al. |
| 2012/0329147 | A1 | 12/2012 | Redford |
| 2013/0203145 | A1 | 8/2013 | Lambert et al. |
| 2014/0045234 | A1 | 2/2014 | Burke |
| 2014/0093924 | A1 | 4/2014 | Moll et al. |
| 2014/0144839 | A1 | 5/2014 | Choi et al. |
| 2014/0186909 | A1 | 7/2014 | Calzia et al. |
| 2014/0315280 | A1 | 10/2014 | Ehwald et al. |
| 2014/0335598 | A1 | 11/2014 | Muller-Feuga et al. |
| 2015/0209783 | A1 * | 7/2015 | Ingber .................... B01D 71/36 96/6 |
| 2015/0230420 | A1 | 8/2015 | Moddemann |
| 2015/0275161 | A1 | 10/2015 | Gressel et al. |
| 2015/0298972 | A1 * | 10/2015 | Ballaguet ............ B01D 53/228 423/575 |
| 2016/0168521 | A1 | 6/2016 | Mottahedeh |
| 2018/0328823 | A1 * | 11/2018 | Olivier ................. B01D 63/087 |
| 2019/0316067 | A1 | 10/2019 | Melchiorri |
| 2020/0248114 | A1 | 8/2020 | Melchiorri |
| 2023/0220319 | A1 | 7/2023 | Melchiorri |

FOREIGN PATENT DOCUMENTS

| | | |
|---|---|---|
| GB | 2339763 A | 2/2000 |
| WO | 20005337 A1 | 2/2000 |
| WO | 2003093406 A2 | 11/2003 |
| WO | 2006020177 A1 | 2/2006 |
| WO | 2008/079724 A2 | 7/2008 |
| WO | 2012177463 A2 | 12/2012 |
| WO | 2015/116963 A1 | 8/2015 |
| WO | 2017/093744 A1 | 6/2017 |

OTHER PUBLICATIONS

Cogne et al. A simple reliable bioreactor for studying the growth and metabolism of photosynthetic micro-organisms in space. No. 2003-01-2419. SAE Technical Paper, 2003.

Cogne et al. "Design, operation, and modeling of a membrane photobioreactor to study the growth of the Cyanobacterium Arthrospira platensis in Space Conditions." Biotechnology Progress 21(3): 741-750 (2005).

Decision of Rejection for CN Patent Application No. 201780074919, issued Apr. 14, 2023, 24 pages [English Translation].

Deng, "Applied Microalgal Biology", Ocean Press (Nov. 30, 2016), 21 pages [English Translation].

Emery et al. "Oxygenation of intensive cell-culture system." Applied microbiology and biotechnology 43(6): 1028-1033 (1995).

Interstate Specialty Products Supplies PDMS Sheets and Membranes. Feb. 3, 2015. Retrieved Dec. 28, 2021. 3 pages.

Jimenez et al. "Relationship between physicochemical variables and productivity in open ponds for the production of Spirulina: a predictive model of algal yield." Aquaculture 221(1-4): 331-345 (2003).

Merkel et al. "Gas sorption, diffusion, and permeation in poly (dimethylsiloxane)." Journal of Polymer Science Part B: Polymer Physics 38.3 (2000): 415-434.

Oren. "A hundred years of Dunaliella research: 1905-2005." Saline Systems 1(1): 2 pp. 1-14 (2008).

PolymersnetBase. "PDMS". Accessed Oct. 27, 2021.

Posten et al., "Microalgae Biotechnology", Springer International Publishing, 205 pages (Dec. 21, 2015).

Qing et al. (Jul. 31, 2008), "Environmental Engineering", Harbin Engineering University Press, 22 pages [English Translation].

Robb "Thin silicone membranes-their permeation properties and some applications." Annals of the New York Academy of Sciences 146.1 (1968): 119-137.

Schneider et al., "Bubble-free oxygenation by means of hydrophobic porous membranes", Enzyme and microbial technology 17(9): 839-847 (Sep. 1, 1995).

Sigma-Aldrich. "Oxidative Stress in Cell Culture." Nov. 1, 2011. Accessed Apr. 26, 2021. https://web.archive.org/web/20111101141318/ https://www.sigmaaldrich.com/life-science/cell-culture/learning-center/media-expert/oxidative-stress.html (Year: 2011).

Velez-Suberbie et al. "Impact of aeration strategy on CHO cell performance during antibody production." Biotechnology progress 29(1): 116-126 (2013).

Xizhuan (Jul. 31, 2013), "A Reader on New Energy Technologies", National Academy of Administration Press.

* cited by examiner

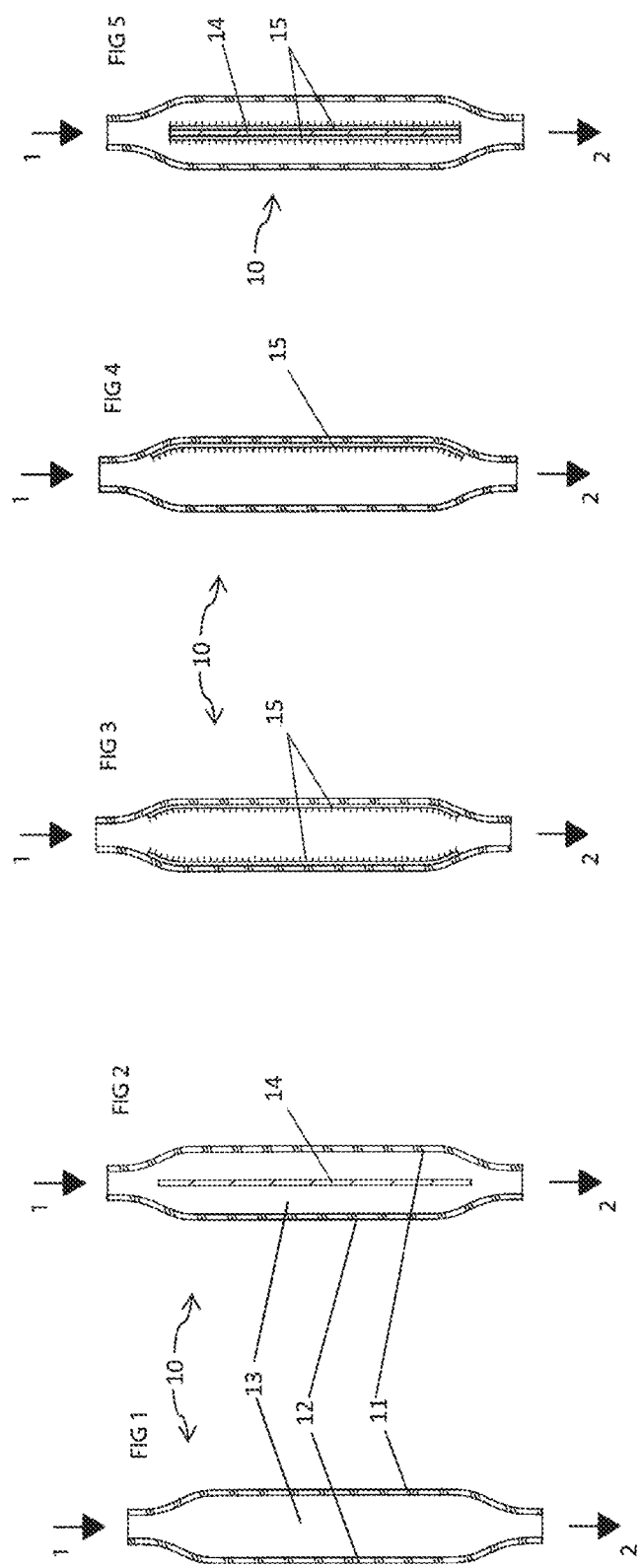

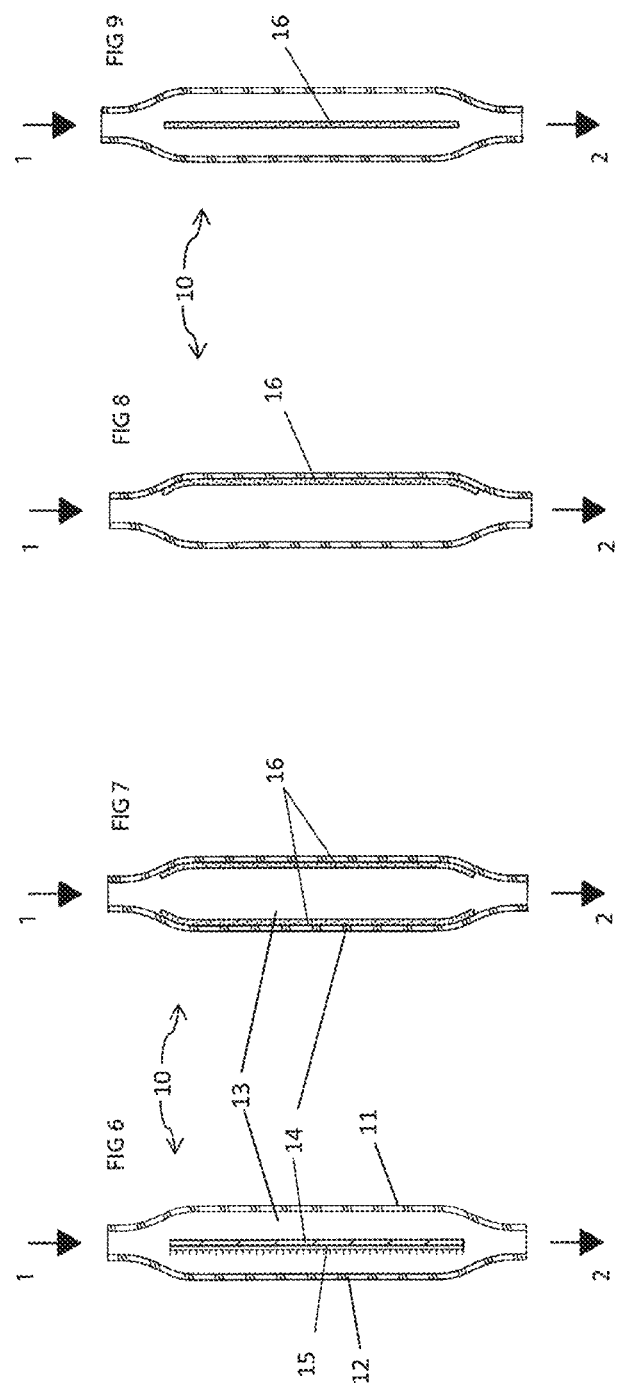

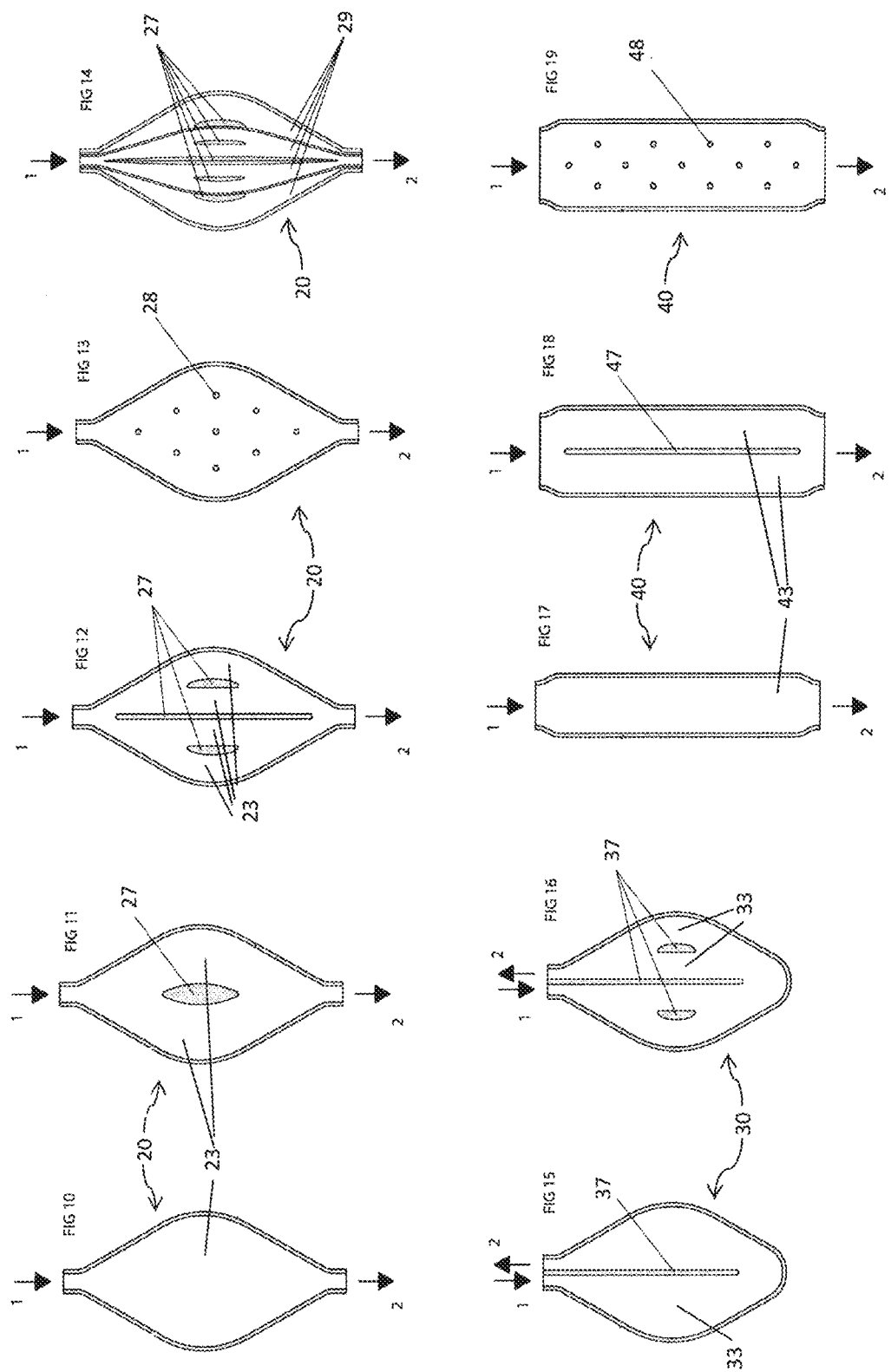

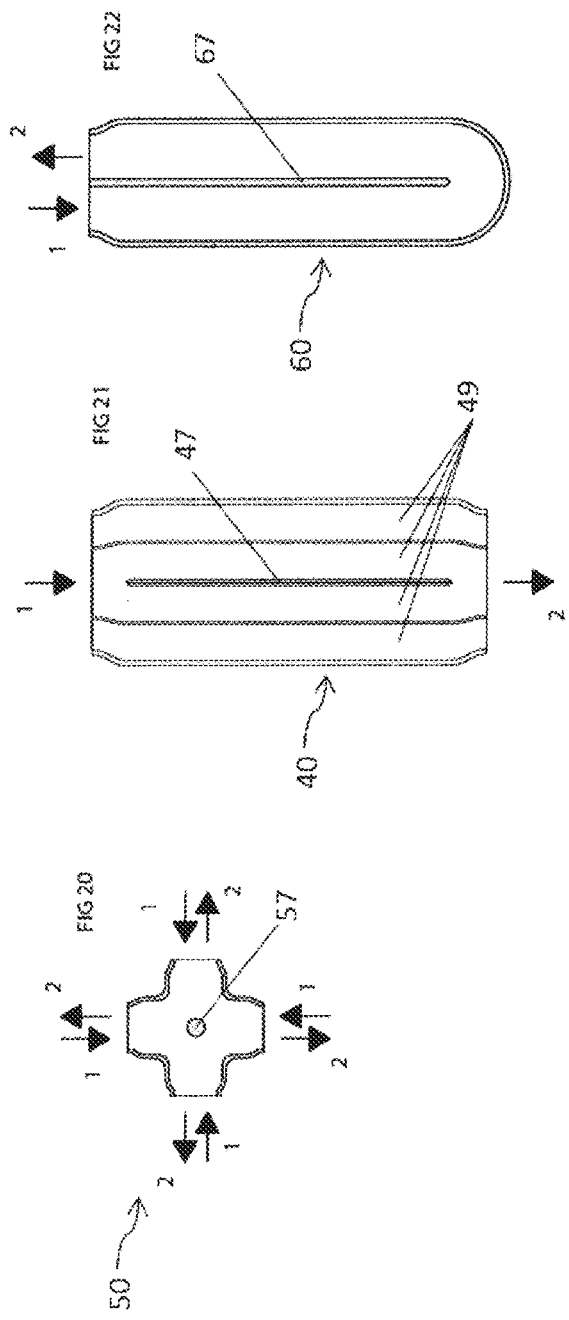
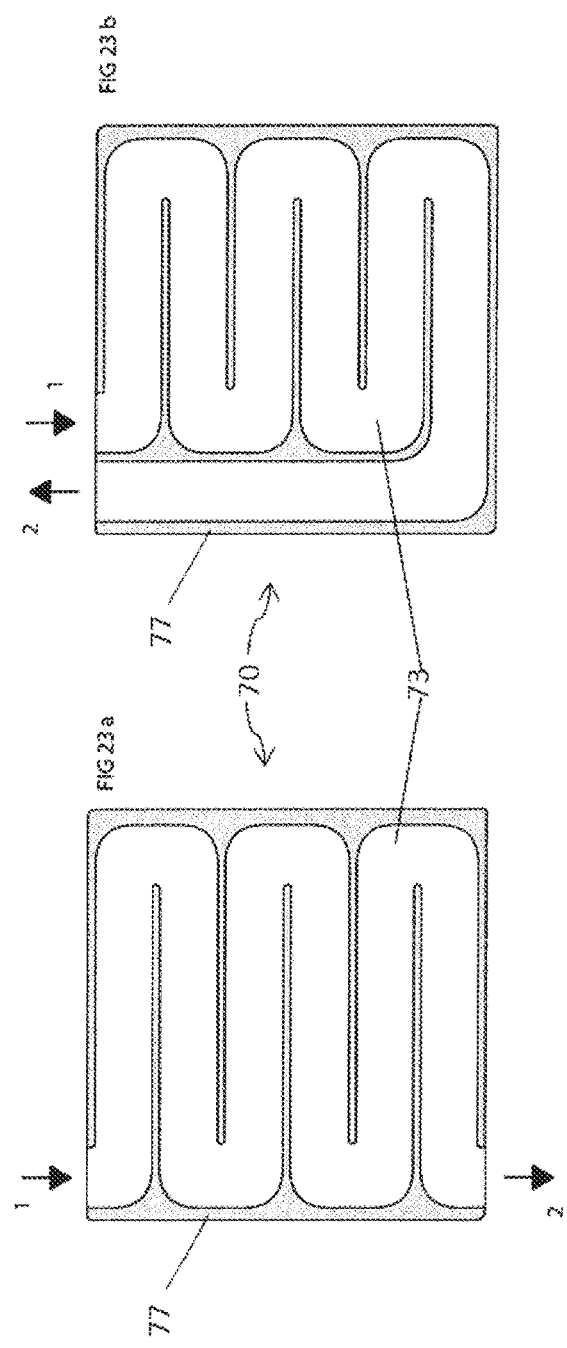

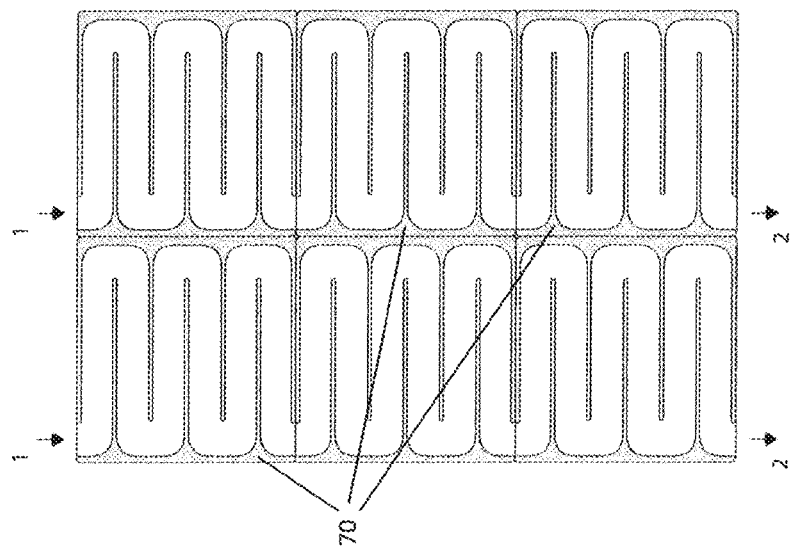
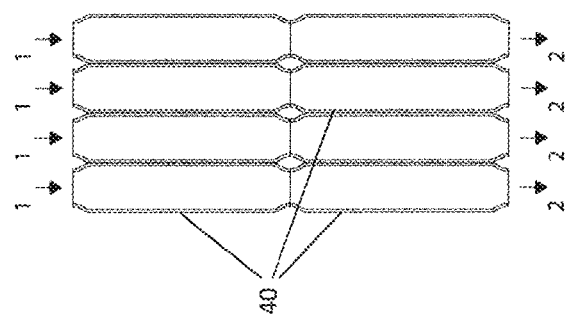
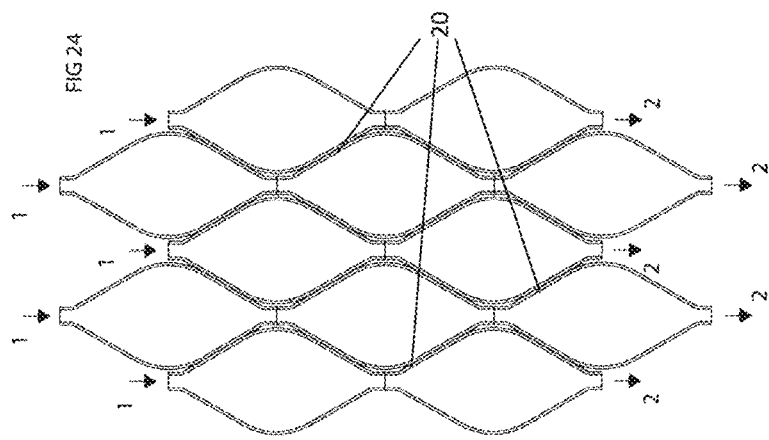

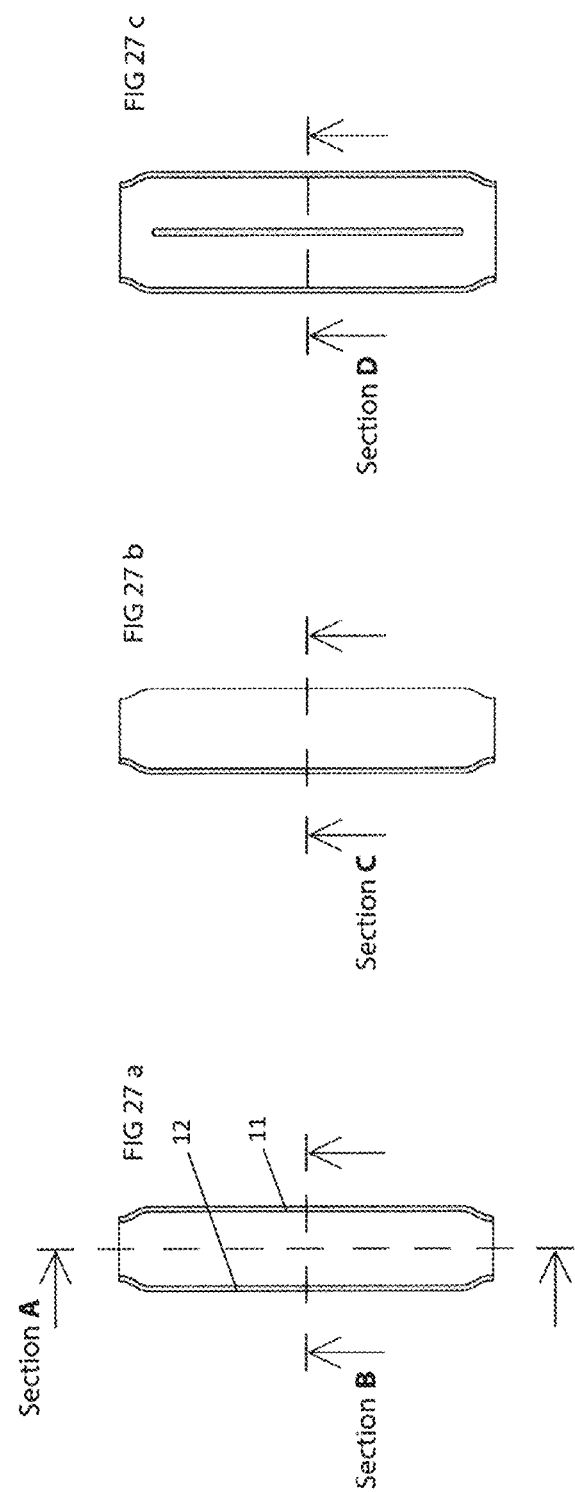

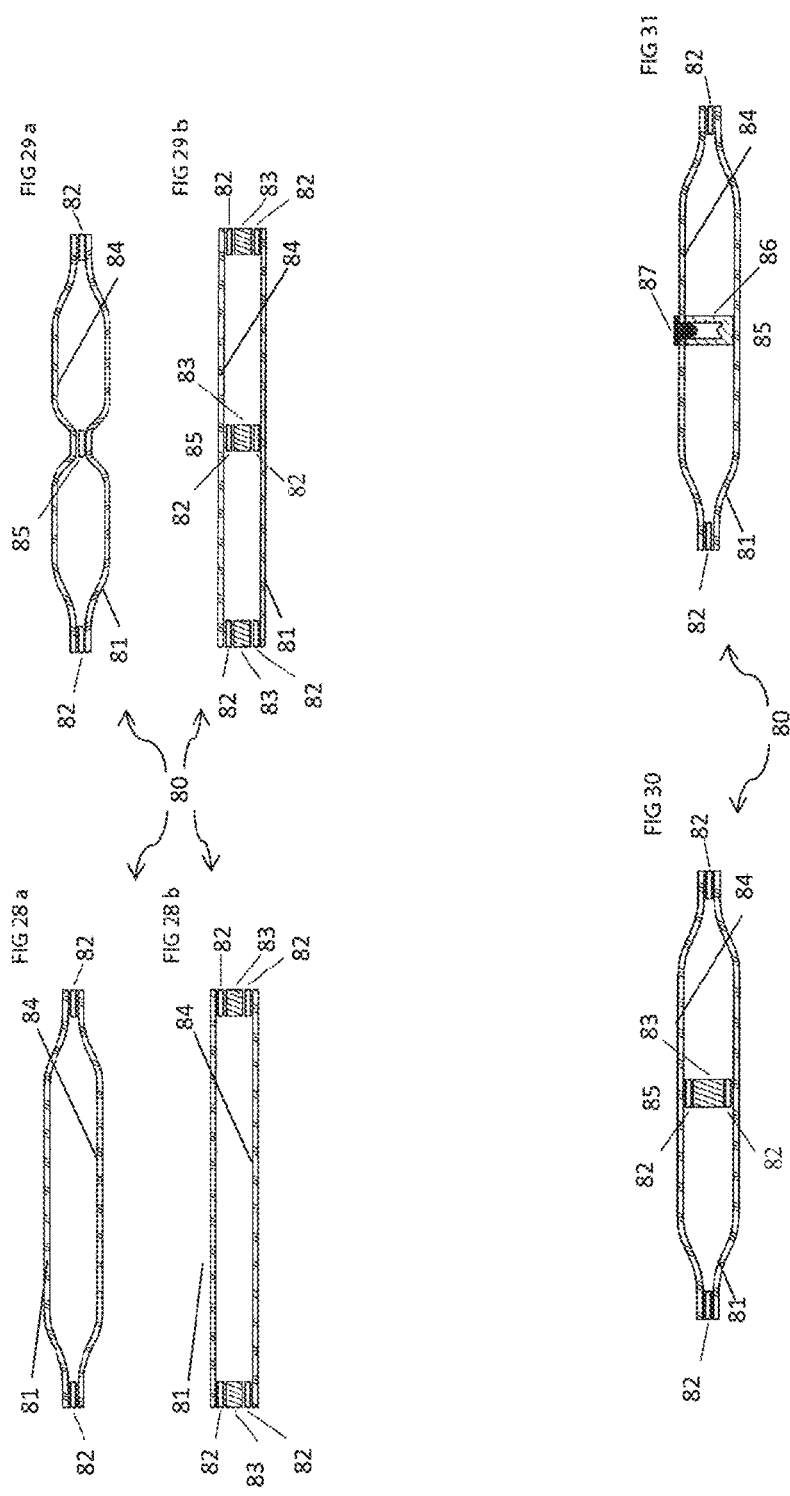

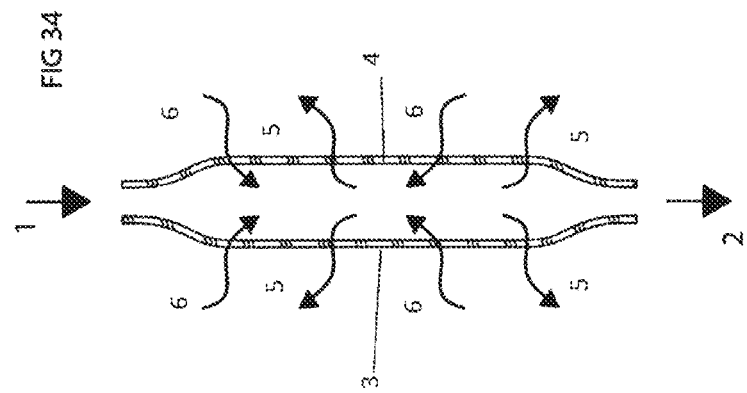
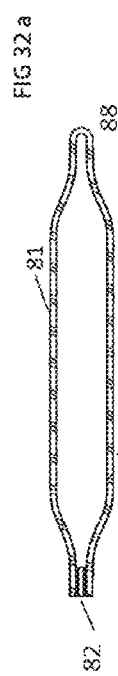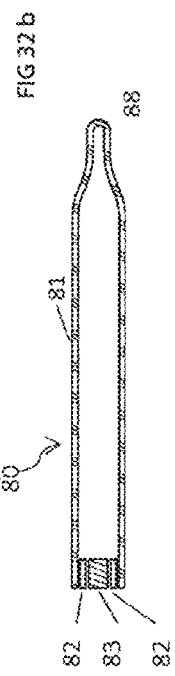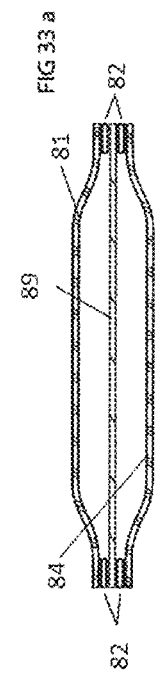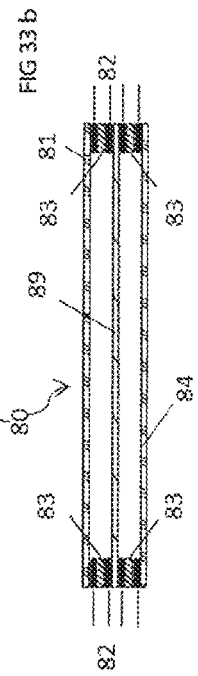

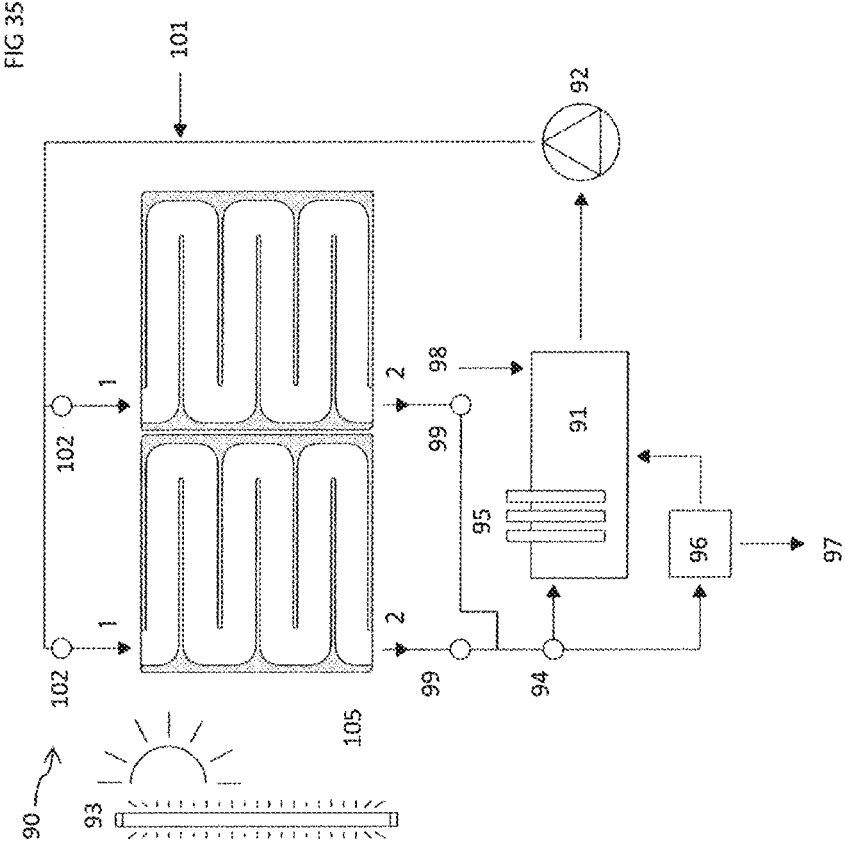

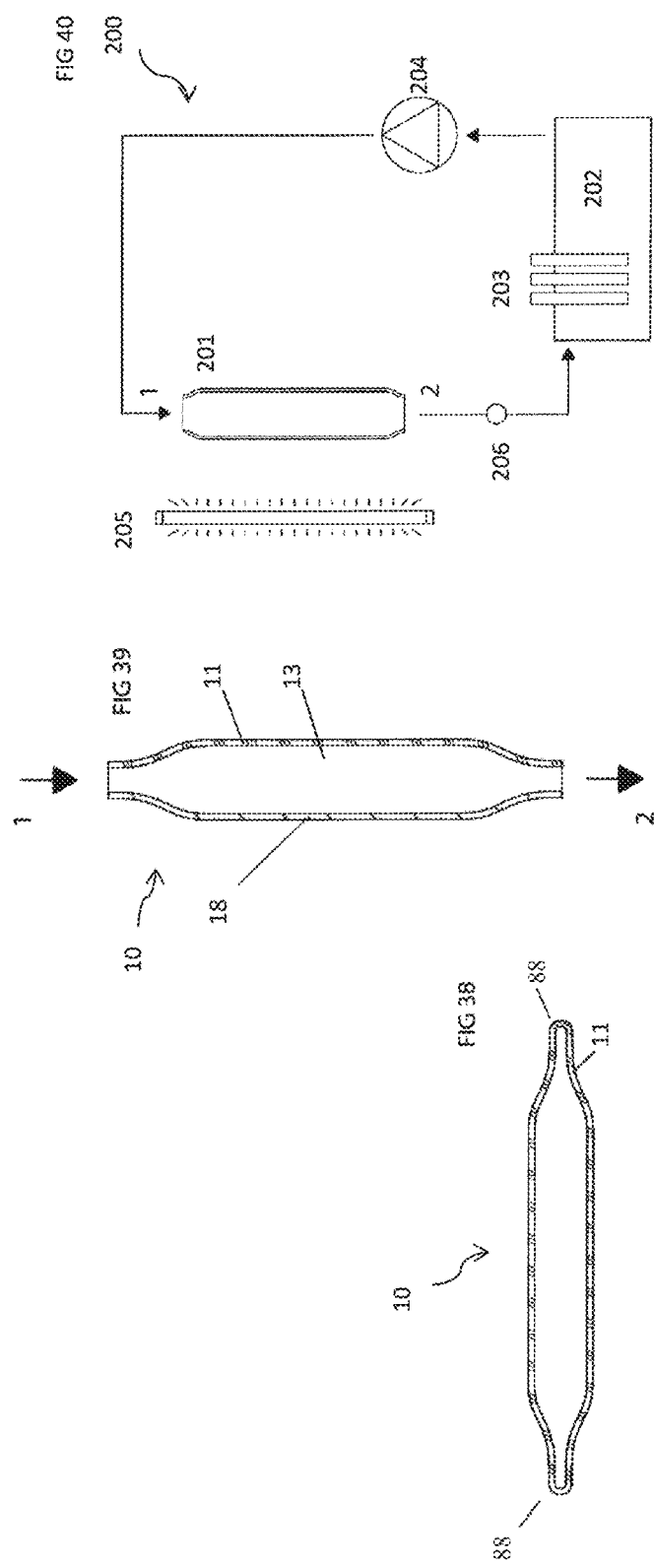

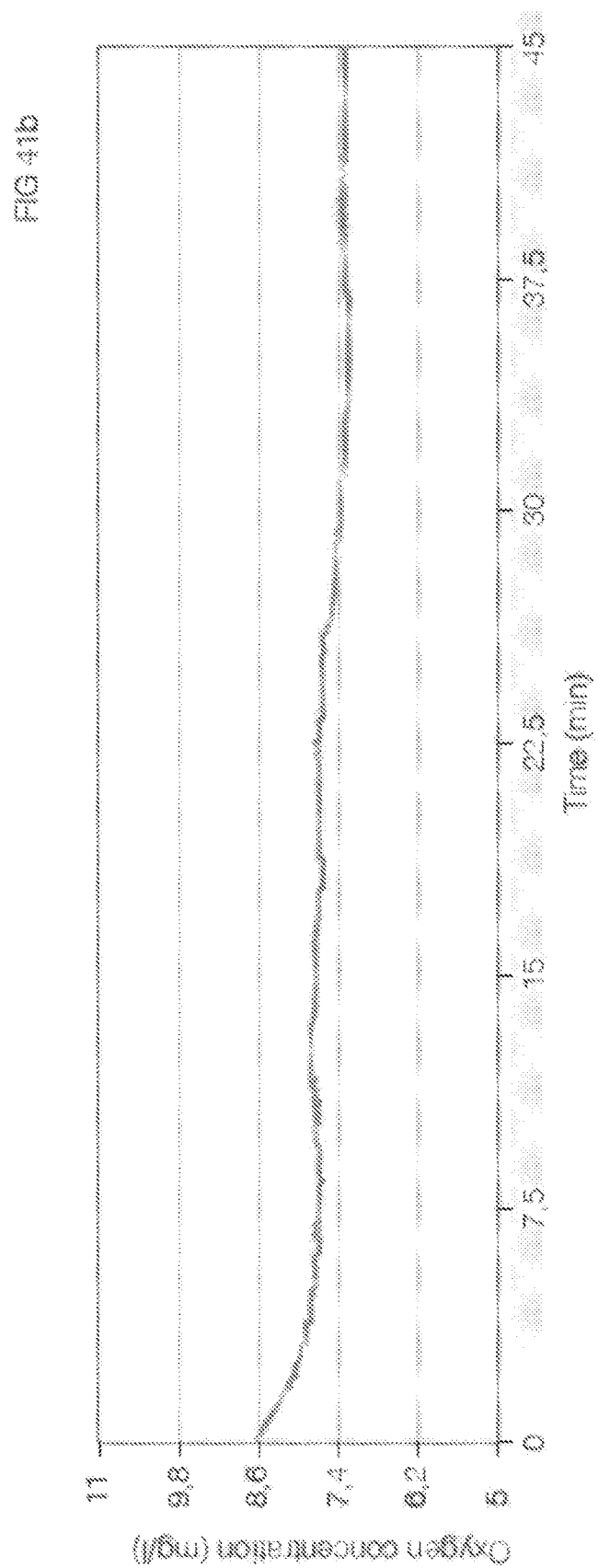

SELECTIVE MEMBRANE-DRIVEN GAS TRANSFER DEVICE AND METHODS

CROSS-REFERENCE TO RELATED APPLICATIONS

This application is a divisional under 35 U.S.C. § 121 of co-pending U.S. Ser. No. 15/780,774 filed Jun. 1, 2018 now abandoned, which is a 35 U.S.C. § 371 National Phase Entry Application of International Application No. PCT/GB2016/053786 filed Dec. 1, 2016, which designates the U.S. and claims benefit under 35 U.S.C. § 119 of G.B. Provisional Application No. 1521136.0 filed Dec. 1, 2015, the contents of which are incorporated herein by reference in their entireties.

FIELD

The present invention relates to photo-bioreactor devices that can be used to generate biomass and assist in environmental remediation. Such devices can also remove gases, such as carbon dioxide and nitrogen oxides, from the environment and can generate oxygen.

BACKGROUND

Due to the global shift away from a reliance on fossil fuel-based energy sources, biomass is becoming increasingly important for energy generation, production of chemicals and other industrial and environmental applications. Biomass derived from non-food sources is of particular interest because it can be produced much faster than other types of land-based agricultural biomass, such as corn and soy, and, once harvested, it can be processed (e.g. by fermentation or refinement) to produce biofuels such as biodiesel, ethanol, butanol and methane (biogas) and/or to produce valuable chemicals and nutrients.

US2014/186909 describes a photobioreactor capsule made by transparent (or semitransparent) flexible polymer films which is divided into a plurality of adjacent channels, in communication with a fluid distribution structure.

GB2339763 describes a photobioreactor of transparent material, comprising a flexible bag with an inlet and an outlet, and a plurality of linear seals defining a plurality of conduits. The flexible bag is made from a non-permeable plastic or polymer.

US2015/0230420 refers to a photobioreactor as well as a biogas unit equipped with such a photobioreactor, which uses a transparent pipe system for the flow-through of a culture suspension, configured in the form of levels in order to enable cultivation over several levels.

DE102012013587 relates to a photo-bioreactor comprising a disposable bag defining a reactor chamber bounded by a wall, and light sources arranged in the immediate vicinity of said wall.

US2014/0093924 describes flat panel biofilm photobioreactor systems with photosynthetic, auto fermentative microorganisms that form a biofilm, and which make chemical products through photosynthesis and subsequent auto fermentation.

WO2015/116963 is concerned with bioreactors defining an essentially closed system except for at least one opening that allows for the introduction of gases and/or nutrients. The gas and/or nutrients are introduced in such a way as to provide mixing and aeration of a cell culture in the bioreactor.

US2009/305389 describes photobioreactors comprising a flexible outer bag, with membrane tubes situated inside the outer bag allowing for introduction of high concentrations of carbon dioxide into the media contained within.

US2011/312084 describes photobioreactors comprising methacrylic polymers in the form of films, plates or cylinders such as tubes.

There is a need for new highly scalable and low cost bioreactors capable of generating large quantities of biomass to meet current energy and environmental challenges. In addition, there exists a need for photobioreactors that facilitate ease of installation, exhibit relatively low running costs and that can contribute to environmental remediation, such as absorption of greenhouse gases or treatment of contaminated water supplies. The present invention seeks to address these and other problems as will become apparent from the disclosure below.

SUMMARY

A first aspect of the invention provides a photobioreactor device comprising:
(i) a photobioreactor unit comprising a first membrane layer and a second membrane layer, the two membrane layers arranged such that at least a portion of the first membrane layer is directly bonded to at least a portion of the second membrane layer in order to form a defined boundary around non-bonded portions of the first and second membrane layers, thereby defining the photobioreactor unit capable of containing a fluid, wherein at least one of the first and second layers is translucent, and
wherein at least a part of the first and second membrane layers is permeable to gases, wherein the permeability coefficient of oxygen through the first and/or second membrane layer is suitably not less than about 100 Barrer, typically not less than about 300 Barrer, and suitably not less than about 400 Barrer; and
(ii) an inlet and an outlet port to enable the fluid to circulate through said unit.

According to embodiments of the invention substantially all of the first membrane layer is permeable to gases. In an alternative embodiment, the second membrane layer is permeable to gases, optionally substantially all of both the first membrane layer and the second membrane are permeable to gases.

In one embodiment of the invention the permeability coefficient of oxygen through the first and/or second membrane layer is suitably not less than about at least 500, at least 650, at least 750, suitably at least 820 Barrers. Suitably at least a part of the first and second membrane layers is permeable to carbon dioxide and the permeability coefficient of carbon dioxide permeability is selected from: not less than at least 1000, at least 2000, at least 2200, at least 2500, at least 2800, at least 2900, at least 3000, at least 3100, at least 3200, at least 3300, at least 3400, at least 3500, at least 3600, at least 3700, at least 3800, suitably at least 3820 Barrers. In a specific embodiment of the invention, at least a part of the first and/or second membrane layers is permeable to other gases including, but not limited to, oxides of nitrogen and methane.

In an embodiment of the invention, at least one of the first and/or second membrane layer comprises a material, which is suitably translucent or even substantially transparent, selected from one of: silicones, polysiloxanes, polydimethylsiloxanes (PDMS), fluorosilicone, and organosilicones. In a specific embodiment, the material comprises polydimethylsiloxanes (PDMS) or elastomers thereof.

In an embodiment of the invention at least one photosynthetic microorganism is comprised within the unit. Suitably the photosynthetic microorganism is selected from: *Haematococcus* sp., *Haematococcus pluvialis*, *Chlorella* sp., *Chlorella autotraphica*, *Chlorella vulgaris*, *Scenedesmus* sp., *Synechococcus* sp., *Synechococcus elongatus*, *Synechocystis* sp., *Arthrospira* sp., *Arthrospira platensis*, *Arthrospira maxima*, *Spirulina* sp., *Chlamydomonas* sp., *Chlamydomonas reinhardtii*, *Geitlerinema* sp., *Lyngbya* sp., *Chroococcidiopsis* sp., *Calothrix* sp., *Cyanothece* sp., *Oscillatoria* sp., *Gloeothece* sp., *Microcoleus* sp., *Microcystis* sp., *Nostoc* sp., and *Anabaena* sp. Optionally the photosynthetic microorganism is selected from *Dunaliella salina* and *Synechococcus marinus*.

In one embodiment the photobioreactor unit further comprises at least one flow control structure. Optionally the photobioreactor unit further comprises at least one biological support.

In a specific embodiment the photobioreactor further comprises an auxiliary system in fluid communication with the photobioreactor unit. Typically the auxiliary system comprises at least one or more of the group consisting of: conduits; reservoirs; pumps; valves; biomass-separators; illumination systems; temperature control systems; sensors; and computers/CPU controllers.

In one embodiment the device comprises a plurality of photobioreactor units. Optionally the plurality of photobioreactor units are in fluid communication with each other and arranged in an array. Suitably the array of photobioreactor units may be configured in series or, alternatively, in parallel.

A second aspect of the invention provides a photobioreactor system comprising:
(a) at least one photobioreactor unit comprising a first membrane layer and a second membrane layer, the two membrane layers arranged such that at least a portion of the first membrane layer is directly bonded to at least a portion of the second membrane layer in order to form a defined boundary around non-bonded portions of the first and second membrane layers, thereby defining the photobioreactor unit capable of containing a fluid,
wherein at least one of the first and second layers is translucent, and
wherein at least a part of the first and second membrane layers is permeable to gases, wherein the permeability coefficient of oxygen through the first and/or second membrane layer is suitably not less than about 100 Barrer, typically not less than about 300 Barrer, and suitably not less than about 400 Barrer; and
an inlet and an outlet port to enable the fluid to circulate through said unit;
(b) a fluid reservoir that is in fluid communication with the inlet and outlet port of the at least one photobioreactor unit;
(c) a pump for maintaining fluid circulation throughout the system; and
(d) a biomass collector.

A third aspect of the invention provides a process for manufacturing biomass comprising culturing a photosynthetic microorganism within a device as set out above, and harvesting the biomass from the device.

A fourth aspect of the invention provides a process for manufacturing biomass comprising culturing a photosynthetic microorganism within a system as set out above, and harvesting the biomass from the system.

A fifth aspect of the invention provides a process for treating wastewater comprising culturing a photosynthetic microorganism within a device as set out above, passing wastewater through the device such that the photosynthetic microorganism within a device removes or remediates toxins from the wastewater.

A sixth aspect of the invention provides a process for removing an atmospheric pollutant comprising culturing a photosynthetic microorganism within a device as set out above, exposing the device to an atmosphere comprising the pollutant such that the photosynthetic microorganism within a device removes or remediates pollutant from the atmosphere.

A seventh aspect of the invention provides a photobioreactor device comprising:
(I) a photobioreactor unit comprising a first membrane layer and a second membrane layer, the two membrane layers arranged such that at least a portion of the first membrane layer is directly bonded to at least a portion of the second membrane layer in order to form a defined boundary around non-bonded portions of the first and second membrane layers, thereby defining the photobioreactor unit capable of containing a fluid,
wherein at least one of the first and second layers is translucent, and
wherein at least a part of the first and second membrane layers comprises a polysiloxane; and
(II) an inlet and an outlet port to enable the fluid to circulate through said unit.

In a specific embodiment of the invention the polysiloxane comprises a polydimethylsiloxane (PDMS) or an elastomer thereof.

In a eighth aspect the invention provides a photobioreactor device comprising:
(i) a photobioreactor unit comprising a first membrane layer and a second membrane layer, the two membrane layers arranged such that at least a portion of the first membrane layer is directly bonded to at least a portion of the second membrane layer in order to form a defined boundary around non-bonded portions of the first and second membrane layers, thereby defining the photobioreactor unit capable of containing a fluid,
wherein at least one of the first and second layers is translucent, and
wherein at least a part of the first and second membrane layers is permeable to gases, wherein the permeability coefficient of carbon dioxide through the first and/or second membrane layer is selected from: not less than at least 1000, at least 2000, at least 2200, at least 2500, at least 2800, at least 2900, at least 3000, at least 3100, at least 3200, at least 3300, at least 3400, at least 3500, at least 3600, at least 3700, at least 3800, suitably at least 3820 Barrers; and
(ii) an inlet and an outlet port to enable the fluid to circulate through said unit.

It will be appreciated that the aspects and embodiments of the invention may be subjected to further combinations of features not explicitly recited above but which are described in detail herein.

DRAWINGS

The invention is further illustrated by reference to the accompanying drawings in which:

FIG. 1 shows a cut-sectional view (Section A of FIG. 27a) of a device according to an embodiment of the invention having first and second membrane layers represented by triple line hatching.

FIG. 2 shows a cut-sectional view (Section A of FIG. 27a) of a device according to an embodiment of the invention wherein both the first and second layers are membrane layers and wherein an additional component is located inside the unit formed by the two layers. Single hatching in the reverse direction indicates the additional component.

FIG. 3 shows a cut-sectional view of a unit according to an embodiment of the invention wherein both the first and second layers are membrane layers and wherein a biological support coats the internal surface of both layers. Grey fill colour represents the biological support coating.

FIG. 4 shows a cut-sectional view of a unit according to an embodiment of the invention wherein both the first and second layers are membrane layers and wherein the internal surface of one membrane layer is coated with a biological support. Dotted fill/small cross indicates the porous additional component.

FIG. 5 shows a cut-sectional view of a unit according to an embodiment of the invention having first and second membrane layers, wherein an additional component is located inside the unit formed by the two membrane layers and wherein the additional component is coated on both sides with a biological support.

FIG. 6 shows a cut-sectional view of a unit according to an embodiment of the invention having first and second membrane layers, wherein an additional component is located inside the unit formed by the two membrane layers and wherein the additional component is coated on one side/surface with a biological support.

FIG. 7 shows a cut-sectional view of a unit according to an embodiment of the invention having first and second membrane layers, wherein the inside surface of each membrane layer is contacted with a porous additional component.

FIG. 8 shows a cut-sectional view of a unit according to an embodiment of the invention having first and second membrane layers, wherein the inside surface of one membrane layer is contacted with a porous additional component.

FIG. 9 shows a cut-sectional view of a unit according to an embodiment of the invention having first and second membrane layers, wherein a porous additional component is located inside the unit formed by the two membrane layers.

FIG. 10 shows a simple front-view streamlined version of the unit according to an embodiment of the invention, having one fluid conduit with an inlet and an outlet located on opposite sides.

FIG. 11 shows a simple front-view streamlined version of the device according to an embodiment of the invention, having two fluid conduits with an inlet and an outlet located on opposite sides of the device and a single control structure.

FIG. 12 shows a front-view streamlined version of the device according to an embodiment of the invention, having multiple fluid conduits. The central portion has both linear and streamlined flow control structures.

FIG. 13 shows a front-view streamlined version of the device according to an embodiment of the invention, having multiple round flow control structures, which create multiple different pathways.

FIG. 14 shows an arrangement that is configured to increase the surface area of the device. There are multiple portions that protrude radially outwardly, each comprising flow control structures as described in FIG. 12.

FIG. 15 shows a representation of a device according to an embodiment of the invention, wherein the inlet and the outlet are located adjacent to each other, on the same side of the device. There is a linear control flow structure, which forms a single channel within the pocket.

Figure 37:
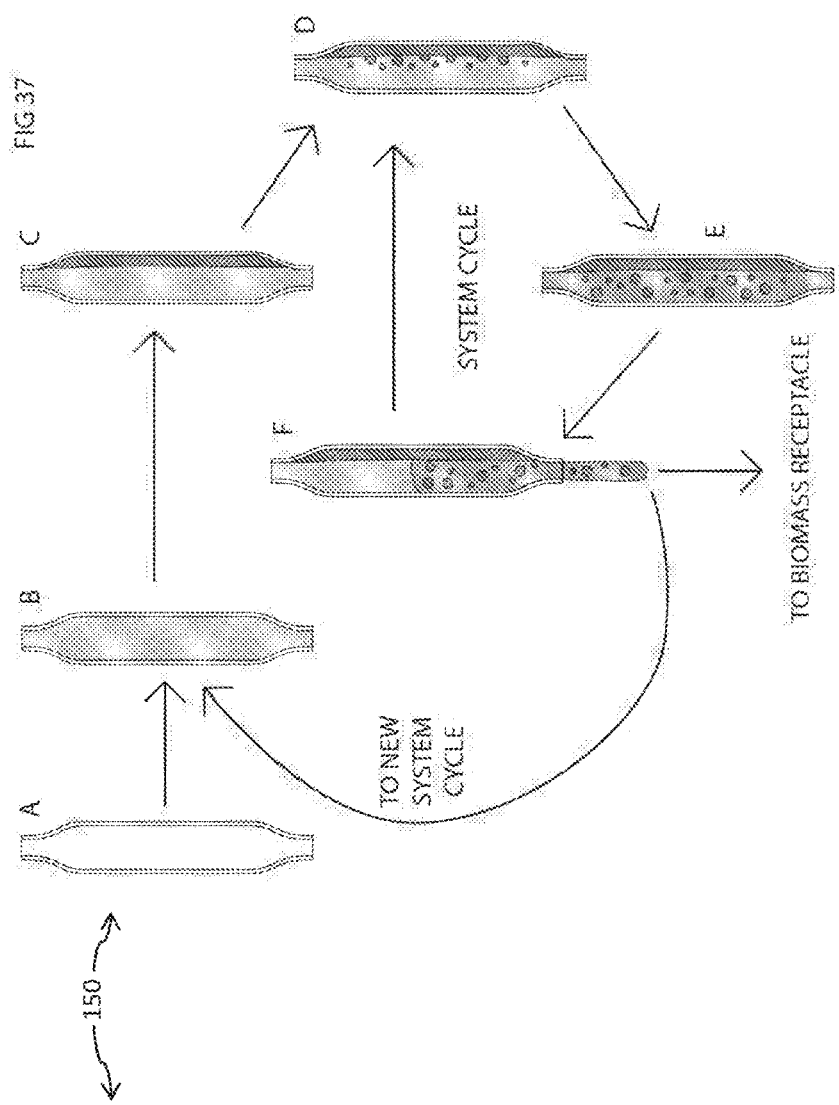

FIG. 16 also shows a version of the device according to an embodiment of the invention in which the inlet and the outlet are located adjacent to each other, on the same side of the device. In this front-view representation of the device, the central portion has both linear and streamlined flow control structures, which create bifurcated channels.

FIG. 17 shows a linear device according to an embodiment of the invention having one fluid conduit with an inlet and an outlet located on opposite sides.

FIG. 18 shows a linear device according to an embodiment of the invention having two fluid conduits with an inlet and an outlet located on opposite sides of the device and a single control structure in the central portion.

FIG. 19 shows a device according to an embodiment of the invention including multiple round flow control structures, which create multiple different pathways.

FIG. 20 shows a version of the device according to an embodiment of the invention having four branches, having multiple openings that function as both inlets and outlets.

FIG. 21 shows an arrangement according to an embodiment of the invention having multiple protruding portions, creating multiple channels.

FIG. 22 shows a linear U-shaped device according to an embodiment of the invention with a single channel created by a linear flow control structure. Both the inlet and the outlet are located on the same side of the device.

FIG. 23a shows a rectangular device according to an embodiment of the invention with a single fluid conduit following a tortuous path created by multiple control structures, having an inlet and an outlet located on opposite sides of the device.

FIG. 23b shows a rectangular device according to an embodiment of the invention with a single fluid conduit following a tortuous curved path created by multiple control structures. Both the inlet and the outlet are located on the same side of the device.

FIG. 24 is an example of a modular array of multiple devices according to an embodiment of the invention comprising streamlined and intercalating devices.

FIG. 25 is an example of a modular array of multiple devices according to an embodiment of the invention comprising linear devices.

FIG. 26 is an example of a modular array of multiple devices according to an embodiment of the invention that are configured to occupy a rectangular space. Each individual device shown in this representation is a device within the scope of the invention.

FIG. 27a shows the planar sections A and B through a representation of a device according to an embodiment of the invention and is included to aid understanding of the other drawings provided herein.

FIG. 27b shows the planar section C through a representation of the device according to an embodiment of the invention having one single membrane layer folded on itself and bonded therefore forming a unit.

FIG. 27c shows the planar section D through a representation of the device according to an embodiment of the invention having a central control structure and is included to aid understanding of the other drawings provided herein.

FIG. 28a shows a cut-sectional view (Section B of FIG. 27a) of a unit according to an embodiment of the invention having first and second membrane layers bonded together through a glue interface.

FIG. 28b shows a cut-sectional view (Section B of FIG. 27a) of a unit according to an embodiment of the invention having first and second membrane layers with a structural component in between where the membranes are bonded to opposing surfaces of the structural component through a glue interface.

FIG. 29a shows a cut-sectional view (Section D of FIG. 27c) of a unit according to an embodiment of the invention having a first and second membrane layers bonded together through a glue interface. The central bonding forms a control structure which creates two fluid conduits.

FIG. 29b shows a cut-sectional view (Section D of FIG. 27c) of a unit according to an embodiment of the invention having a first and second membrane layers with a structural component in between where the membranes are bonded to opposing surfaces of the structural component through a glue interface. The central bonding forms a control structure which creates two fluid conduits.

FIG. 30 shows a cut-sectional view (Section D of FIG. 27c) of a device according to an embodiment of the invention representing a mixed composition of bonding techniques.

FIG. 31 shows a cut-sectional view (Section D of FIG. 27c) of a device according to an embodiment of the invention, wherein an artificial light-source is embedded inside the device and specifically inside a control structure (indicated by single and dashed line hatching) located between the first and second membrane layers.

FIG. 32a shows a cut-sectional view (Section C of FIG. 27b) of a device according to an embodiment of the invention, wherein the unit is composed of a single tube-like shaped membrane layer extrusion which is folded over and bonded to itself at one end through a glue interface.

FIG. 32b shows a cut-sectional view (Section C of FIG. 27b) of a device according to FIG. 32a, having a folded configuration and a structural component inserted where the membrane is bonded to itself through a glue interface.

FIG. 33a shows a cut-sectional view of a unit according to an embodiment of the invention having first and second membrane layers, wherein an additional component is located inside the unit formed by the two membrane layers.

FIG. 33b shows a cut-sectional view of a unit according to FIG. 33a, having a structural component inserted between the membranes, which are bonded through a glue interface.

FIG. 34 shows a cut-sectional view of a unit according to an embodiment of the invention having first and second membrane layers, and representing directions of gas permeation through the membrane layers.

FIG. 35 shows a schematic of an auxiliary system according to an embodiment of the invention which controls a single device's generation and harvesting of biomass.

Figure 36:
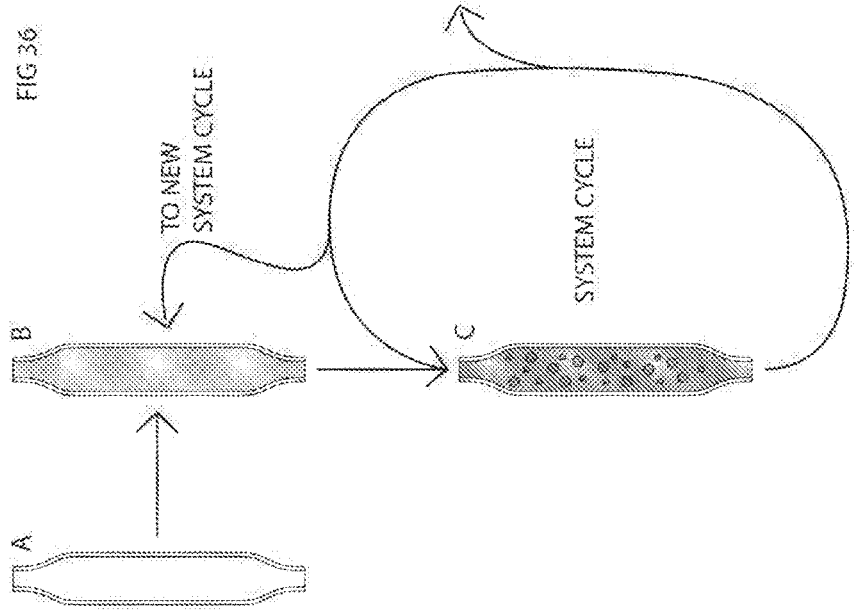

FIG. 36 is an illustration of a cycle of generating and harvesting biomass (either on a continuous or batch basis) using the device according to an embodiment of the invention.

FIG. 37 is an illustration of a cycle of generating and harvesting biomass (either on a continuous or batch basis) using the device according to an embodiment of the invention.

FIG. 38 shows a cut-sectional view (Section B of FIG. 27a) of a device according to an embodiment of the invention, wherein the unit is composed of a single tube-like shaped membrane layer extrusion.

FIG. 39 shows a cut-sectional view (Section A of FIG. 27a) of a device according to an embodiment of the invention having a membrane layer and a non-membrane layer.

FIG. 40 shows a schematic of a system according to an embodiment of the invention described in the example.

Figure 41A:
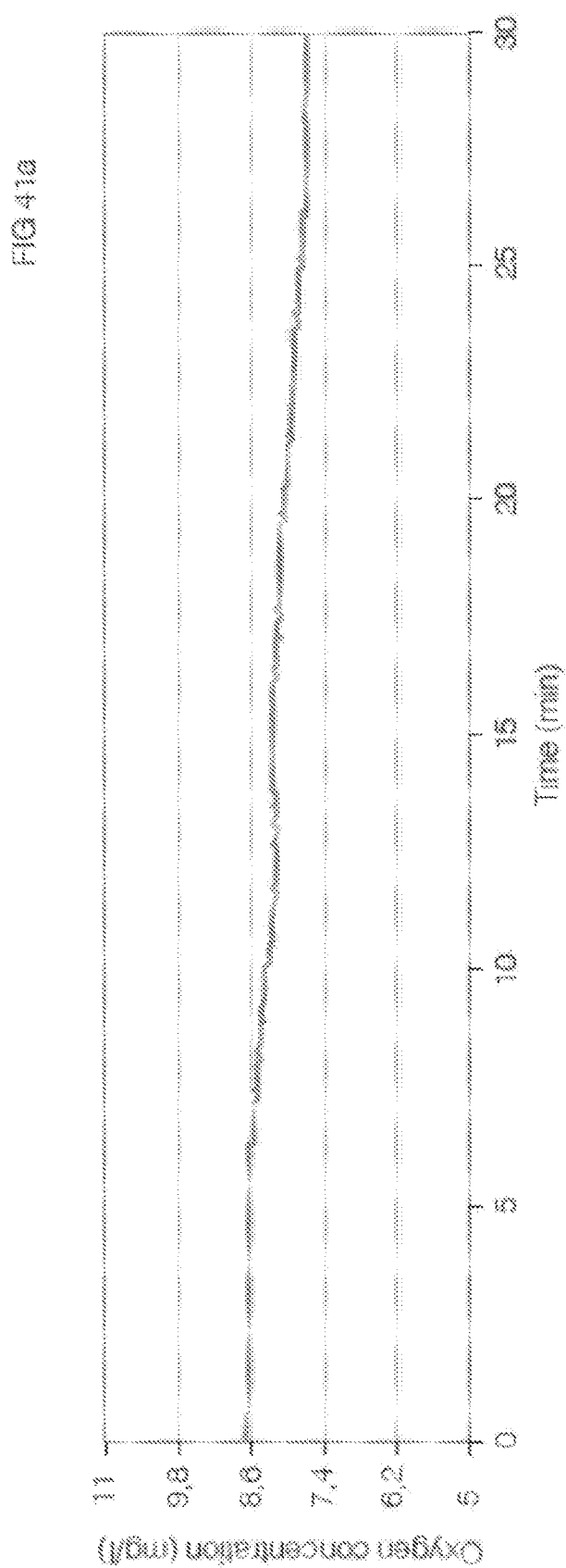

FIG. 41a shows the results of the example in the form of a graph of oxygen concentration in the liquid medium for the first experimental run (Run A).

FIG. 41b shows the results of the example in the form of a graph of oxygen concentration in the liquid medium for the second experimental run (Run B).

DETAILED DESCRIPTION

All references cited herein are incorporated by reference in their entirety. Unless otherwise defined, all technical and scientific terms used herein have the same meaning as commonly understood by one of ordinary skill in the art to which this invention belongs.

The present inventors have developed a gas permeable photobioreactor device suitable for generating biomass. Advantageously, biomass can be generated continuously within the device and can be continuously harvested. The quantity of biomass generated can be increased or optimised, for example by combining a plurality of units in a modular manner or by optimising the shape and/or thickness of the device and its components or by utilising different microorganisms. In addition, embodiments of the invention can also be used to facilitate controlled transfer of gases such as oxygen and/or carbon dioxide between the outside atmosphere and the liquid media inside the unit, used to grow the microorganisms.

The embodiments of the invention are optimised to maximise the photosynthetic efficiency of the photosynthetic microorganisms contained within it, and hence to maximise the efficiency of generation of biomass.

Prior to further setting forth the invention, a number of definitions are provided that will assist in the understanding of the invention.

As used herein, the term "comprising" means any of the recited elements are necessarily included and other elements may optionally be included as well. "Consisting essentially of" means any recited elements are necessarily included, elements that would materially affect the basic and novel characteristics of the listed elements are excluded, and other elements may optionally be included. "Consisting of" means that all elements other than those listed are excluded. Embodiments defined by each of these terms are within the scope of this invention.

As the skilled person will be aware, the term "photosynthesis" refers to a biochemical process that takes place in green plants and other photosynthetic organisms, including photosynthetic microorganisms including algae and cyanobacteria. The process of photosynthesis utilises light to convert carbon dioxide and water to metabolites and oxygen. As used herein, the term "photosynthetic microorganism" refers to any microorganism that is capable of photosynthesis. As used herein, the related terms "phototrophic" and "photosynthesising" are synonymous with to "photosynthetic" and the two terms can be used interchangeably herein.

As used herein, the term "translucent" has its ordinary meaning in the art, and refers to a light-pervious material that allows light to pass through, resulting in the random internal scattering of light rays. The term is synonymous with "semi-transparent".

As used herein, the term "transparent" has its ordinary meaning in the art, and refers to a material that allows visible light to pass through it, such that objects can be clearly seen on the other side of the material, in other words it can be described as "optically clear". All membrane and non-membrane materials, additional components, control structures, coatings and other materials described herein can be substantially translucent or substantially transparent.

As used herein, the term "permeable" or "gas permeable" means a material that allows gases, in particular oxygen ($O_2$), carbon dioxide ($CO_2$), nitrogen ($N_2$) and, optionally, methane ($CH_4$) to be transferred from one side of the material to the other, in either or both directions. As used herein, the related terms "breathable" and "semipermeable" are synonymous with "permeable" and the two terms can be used interchangeably herein. Typically, the material is in the form of a sheet, film or membrane. The permeation is directly related to the concentration gradient of the permeant (such as gas), a material's intrinsic permeability, and the diffusivity of the permeant species in the membrane material.

Permeability of a gas through a specific material is measured herein in Barrers. The Barrer measures the rate of a gas flow passing through an area of material with a thickness, driven by a given pressure. Barrer is usually calculated at 23° C. (+−2° C.) and is defined as:

$$1\ \text{Barrer} = 10^{-10} \frac{\text{cm}^3_{STP} \cdot \text{cm}}{\text{cm}^2 \cdot \text{s} \cdot \text{cmHg}}$$

It will be appreciated that the Barrer is the most common measurement of gas permeability in current usage, particularly in relation to gas-permeable membranes, however permeability may also be defined by other units examples of which include $\text{kmol} \cdot \text{m} \cdot \text{m}^{-2} \cdot \text{s}^{-1} \cdot \text{kPa}^{-1}$, $\text{m}^3 \cdot \text{m} \cdot \text{m}^{-2} \cdot \text{s}^{-1} \cdot \text{kPa}^{-1}$, or $\text{kg} \cdot \text{m} \cdot \text{m}^{-2} \cdot \text{s}^{-1} \cdot \text{kPa}^{-1}$. ISO 15105-1 specifies two methods for determining the gas transmission rate of single-layer plastic film or sheet and multi-layer structures under a differential pressure. One method uses a pressure sensor, the other a gas chromatograph, to measure the amount of gas which permeates through a test specimen. Other equivalent measurements of gas-permeability are known to the skilled person and would be readily equivalent to Barrer measurements described herein.

As used herein, the terms "porous" and "non-porous" refer to the porosity of a material as a means of classifying the mechanism by which penetrants permeate through the material. Membrane materials are referred to as porous if the gas particles migrate through direct movement through a microporous structure and as non porous if transport of the permeant species from one side of the membrane to the other occurs through more complex physical/chemical mechanisms.

As used herein, the term "biomass" refers to any living or dead microorganism, including any part of a microorganism (including metabolites and by-products expelled by the microorganism). In the context of the present invention, the term "biomass" includes, in particular, the synthetic products of photosynthesis, as described above.

As used herein, the term "sorptivity" has its usual meaning in the art and is a measure of the tendency of a material to absorb and transmit water and other liquids by capillarity. A related term, "hygroscopic" also refers to the ability of a substance to attract and hold water molecules from the surrounding environment. The two terms can be used interchangeably herein.

As used herein, the term "biofilm" refers to a group of microorganisms in which cells attach to each other on a surface.

As used herein, the term, "pocket" also refers to "unit" and the two terms can be used interchangeably herein.

As used herein, the a "device" may be comprised of one "unit" or "pocket", or may comprise an array or combination of a plurality of "units" or "pockets".

As used herein, the term "fluid" refers to a flowable material, typically a liquid and suitably liquid media, which is comprised within the units, and thus the devices of the invention.

As used herein, the term "liquid media" has its usual meaning in the art and is a liquid used to grow the microorganisms and which contains the microorganisms. The liquid media can be comprise one or more of the following: fresh water, salty water, saline, brine, sea water, waste water, nutrients, phosphates, nitrates, vitamins, minerals, micronutrients, macronutrients, metals, microorganisms growth medias, BG11 growth media, and microorganisms.

Similarly the related terms "water channel", "fluid channel", "fluid conduit", "liquid media conduit" and "liquid media channel" are synonymous and the terms can be used interchangeably herein.

As used herein, the related terms "photo-bioconverter" and "photo-bioreactor" are synonymous and the two terms can be used interchangeably herein.

The Outer Layers

According to one embodiment of the invention, a device is provided that comprises a unit which includes outer layers that are membrane layers. One membrane layer may be flexible, although, according to a typical embodiment, both membrane layers are flexible. At least a part of one of the membrane layers, and optionally both the first membrane layer and the second membrane layer, is highly permeable to transmission of gases across the membrane. The permeability coefficient of oxygen through the membrane is not less than about 100 Barrer, typically about 300 Barrer, and suitably about 400 Barrer. In a specific embodiment of the invention the permeability coefficient of oxygen through the membrane is not less than about 500 Barrer and possibly higher. The permeability coefficient of carbon dioxide through the membrane is not less than about 1000 Barrer, suitably about 2500 Barrer, and typically about 3000 Barrer. In a specific embodiment of the invention the permeability coefficient of carbon dioxide through the membrane is not less than about 3200 Barrer. As used in this context, the phrase "at least a part" means an area of the layer that is of a sufficient size to allow a gas to pass through the outer layer of the unit. The gas is typically oxygen and carbon dioxide, but not limited thereto, and may comprise nitrogen, nitrogen oxides, sulphur oxides and/or methane.

The device may be illuminated from a single direction or from multiple directions. If the device is positioned such that it receives light primarily from a single direction and one (first) membrane layer is less transparent or less translucent than the other (second) membrane layer, the first membrane layer can be on the side of the device facing the primary light source. In a particular embodiment, the first membrane layer is located on the side of the device facing away from the light source.

Typically, the membrane layer is at least translucent, and is suitably substantially transparent.

Typically, a membrane layer comprises one or more gas permeable materials. It is important that the gas permeable material is not permeable to liquids, this to prevent liquid media inside the unit leaking to the outside of the unit. The gas permeable material can be porous (including microporous structure gas permeable materials) or non-porous. Gas permeable materials are referred to as porous if the gas particles can migrate through direct movement through a microporous structure. If the gas permeable material is porous, it is important that it is substantially impermeable to liquids. Suitably, the gas permeable material is non-porous, this to avoid also liquid permeation through the gas permeable material and to avoid lower transparencies which could relate to the porosity of the material.

The gas permeable material may be a polymer, such as a chemically-optimised gas permeable polymer. Chemically-optimised polymers may be advantageous over corresponding unmodified polymers because they may be cheaper, more resistant to tear, hydrophobic, antistatic, more transparent, easier to fabricate with, less brittle, more elastic, more permeable to gases and selectively permeable to specific gasses. Chemical modifications on polymers may be performed in any way a skilled person will know such as by modifying the chemical composition of the monomer, the back bone chain, side chains, end groups, and/or the use of different curing agents, crosslinkers, fillers, processes of vulcanisation, manufacture, fabrication, and other methods.

The membrane layer can comprise any suitable gas permeable material including, but not limited to: silicones, polysiloxanes, polydimethylsiloxanes (PDMS), fluorosilicone, organosilicones, cellulose (including plant cellulose and bacterial cellulose), cellulose acetate (celluloid), nitrocellulose, and cellulose esters.

In a suitable embodiment, the membrane layer comprises polysiloxanes, optionally optimised polysiloxanes. The polysiloxanes may be chemically-modified or machine-modified. Typically, the membrane layer comprises polysiloxane elastomers. It has been found that polysiloxanes are good candidates for gas permeable membranes also thanks to the Si—O bonds into the polymer structure which facilitates higher bond rotation, increasing chain mobility, therefore increasing levels of permeability. As well polysiloxane elastomers (such as silicone rubber) are flexible, tolerant to UV radiation and resilient materials.

In an embodiment, the membrane layer comprises polydimethylsiloxanes (PDMS), suitably optimised polydimethylsiloxanes. Typically the membrane layer comprises polydimethylsiloxane (PDMS) elastomers. Polydimethylsiloxanes (PDMS) can take form of an elastomer, a resin, or a fluid. The PDMS elastomer is formed using a cross-linking agent. PDMS is a typical gas permeable material because of its very high oxygen and carbon dioxide permeability, its optical transparency and its tolerance to UV radiation. These elastomers typically do not support microbiological growth on their surface, and so avoid uncontrolled biofilm growth and/or biofouling which can reduce the efficacy of the device to generate biomass (shielding light). Optionally a biofilm growth can be facilitated by utilising biological supports and/or additional components as described below. Additionally, polydimethylsiloxanes (PDMS) elastomers are flexible and resilient materials.

The polydimethylsiloxanes (PDMS) may be chemically-modified or machine-modified to increase its gas permeability and/or to change its properties. PDMS elastomers typically have an oxygen permeability of at least 350, at least 400, at least 450, at least 550, at least 650, at least 750, suitably at least 820 Barrers and a carbon dioxide permeability of at least 2000, at least 2500, at least 2600, at least 2700, at least 2800, at least 2900, at least 3000, at least 3100, at least 3200, at least 3300, at least 3400, at least 3500, at least 3600, at least 3700, at least 3800, suitably at least 3820 Barrers. The properties of the PDMS used in embodiments of this invention can be optimised through chemical, mechanical and process-driven interventions related to but not limited to the molar mass (Mm) of polymer chains, the dispersity in the polymer (dispersity is the ratio of the weight average molar mass to number average molar mass), the temperature and duration of the heat treatment during curing, the ratio of the cross-linking agent to PDMS, the cross-linking agent chemical composition, different end groups (such us methyl-, hydroxy- and vinyl-terminated PDMS) which can influence the way in which end-linked PDMS structures form during cross-linking.

In another embodiment, the membrane layer comprises bacterial cellulose. While bacterial cellulose has the same molecular formula as plant cellulose, it has significantly different macromolecular properties and characteristics. In general, bacterial cellulose is more chemically pure, containing no hemicellulose or lignin. Furthermore, bacterial cellulose can be produced on a variety of substrates and can be grown to virtually any shape, due to the high moldability during formation. Additionally, bacterial cellulose has a more crystalline structure compared to plant cellulose and forms characteristic thin ribbon-like microfibrils, which are significantly smaller than those in plant cellulose, making bacterial cellulose much more porous. The skilled person will be aware of a number of bacterial systems that are engineered to optimise cellulose production, such as the cellulose biosynthetic system of *Acetobacter* sp., *Azotbacter* sp., *Rhizobium* sp., *Pseudomonas* sp., *Salmonella* sp., and *Alcaligenes* sp., which can be expressed in *E. coli*, for example. Bacterial cellulose can be treated such that its surface provides a chemical interface to enable bonding with molecules.

The second layer may also be a membrane layer—i.e. gas permeable layer—as defined above, or it may be comprised of a non-membrane layer, comprising any suitable material, such as a natural or synthetic material. Suitably, the second layer is at least translucent, and is typically transparent. The second layer is suitably breathable.

In a typical embodiment, both the first and second layers are gas permeable membrane layers as defined herein.

In embodiments wherein the second layer is a non-membrane layer, it may have or have been processed or machined to have a rough or porous surface. This enables microbes to attach to the material and facilitates the development of a biofilm on the inner surface of the layer.

The non-membrane layer can be comprised of any suitable material. The material may have, or may have been treated or modified to produce, a rough or porous surface.

In a suitable embodiment, the first and second layers are bonded by adhesion and/or heat pressing. Heat pressing utilises the application of heat and pressure for a pre-determined period of time so as to form a weld. The skilled person in the art will be familiar with suitable heat pressing techniques for this application. The precise temperature and duration required to bond portions of the first and second layers together will depend on the specific materials comprised in the two layers. Alternatively or additionally, a glue interface can be used to bond portions of the two layers together; once applied on the layers the glue interface can be cured utilising heat pressing techniques, or can cure spontaneously at room temperature or can cure using heat or pressure alone. As used herein, the term "glue interface" also includes the use of non-crystallised (non-vulcanised) polymers that can bond the two layers with heat or humid pressing. As used herein, the related terms, "glue interface", "adhesive" and "adhesive interface" are synonymous, and the three terms can be used interchangeably herein.

The glue interface thickness varies depending on its composition, material and the layer material. Suitably, the glue interface thickness is no less than 10 microns, suitably 20 microns, typically 50 microns. Typically, the glue interface thickness is no more than 5 mm, optionally 1 mm, suitably 600 microns, typically 200 microns.

More specifically, if the first and second layers are comprised of polysiloxanes and/or dimethylpolysiloxanes (PDMS), the two layers can be bonded together by using silicone adhesives which can be in viscous liquid gel form, a layer form, a layer tape form, and/or can comprise all types of silicone adhesive which can cure below or above 22° C. After applying the silicone adhesive on both layers, the bonding areas are typically pressed for a determined period of time as dictated by the type of silicone adhesive and, if the type of silicon adhesive used also needs heat to cure, it is heated at a determined temperature and for a determined period of time as dictated by the type of silicone adhesive which is utilised.

Types of possible silicone adhesives include, but are not limited to, silicone glues and silicone adhesive layers such as the VVB Birzer ADT-X (which bonds with heat pressing for 30 to 60 seconds at pressures between 1 and 15 N/cm$^2$ and temperatures between 140 and 180° C.) with thicknesses between 0.20 mm and 0.60 mm, the Adhesives Research Arclad® IS-7876 silicone transfer adhesive (which is a pressure-sensitive adhesive which bonds with pressure and temperatures above ~5° C.) with thicknesses between 25 and 100 microns. Alternatively the silicon adhesive interface can be composed of a thin layer of un-cured polysiloxane and/or dimethylpolysiloxane (PDMS), which can be mixed with its cross-linking agent, and quickly applied on the intended bonding regions on the layers, then pressed and heated to cure, bonding the two layers together.

In some embodiments, the "glue interface" and/or silicone adhesive can be used to bond the two layers together in the region where the fluid conduit is typically located. This bonding will create a control structure to control the flow of the liquid media, dividing or diverting the fluid conduits in multiple conduits. The control structures/bonded regions increase the structural integrity of the device, facilitate liquid media flow, and increase the control of the device volume, thickness and shape when the unit is inflated by fluid pressure.

In some embodiments, a "structural component" can be placed between the two layers on the bonding regions to reinforce the overall unit structure and to better control the unit thickness and shape when the unit is inflated. These structural components will have thickness equal to the intended unit thickness, and their length and profile shape will follow the intended bonding profile and shape, at least partially. The structural component can be bonded to the two layers by adhesion and/or heat pressing. The precise temperature and duration required to bond portions of the first and second layers to the structural component will depend on the specific materials used of the two layers and of the structural component. Alternatively or additionally, a glue interface can be used to bond portions of the two layers to the structural component.

The material of the structural component can include but is not limited to flexible polymers such as silicones, polysiloxanes, polysiloxane elastomers, polydimethylsiloxanes (PDMS) and PDMS elastomers, and rigid polymers, including optically transparent rigid polymers.

Alternatively or additionally, a glue interface can be used to bond portions of the two layers together with the structural component in between the two layers on the intended bonding regions. Once the glue interface is applied on the layers and on the structural component the glue interface can be cured utilising heat pressing techniques or can cure spontaneously at room temperature or can be cured using heat or pressure alone.

In some embodiments, the structural component, bonded to the two layers with or without a glue interface, can be used to bond the two layers together in the region where the fluid conduit is typically located. This bonding creates a control structure to control the flow of the liquid media dividing the fluid conduit in multiple fluid conduits. The control structures/structural component-bonded regions increase the structural integrity of the device, facilitate liquid media flow, and/or increase the control of the device volume, thickness and shape when the unit is inflated by fluid pressure.

The glue interface and the structural component are suitably translucent and typically transparent.

In a suitable embodiment, the unit can be made of a single sheet of gas permeable membrane layer folded over on itself and the two ends of the single sheet can be bonded thereby defining a unit. The bonding methods are the same as described above. Other bonding between the two sides of the folded layer can be present to create control structures as described above. The folded edge can function as a fixing point to a mounting structure or manifold; the folded edge can also be clamped or otherwise reinforced.

In an embodiment, the unit can be made of a single sheet of gas permeable membrane that is extruded in a tube-like shape. In this embodiment there is no need to bond the ends because it is already closed on two sides, thereby defining the unit. Bonding between the two sides of the same extruded layer can however be present to create control structures as described above. The edges can function as a fixing point to a mounting structure; the folded edge can also be clamped or reinforced.

Additional Component

In some embodiments, the device of the invention comprises an additional component (e.g. 14, 16 etc.) located within the pocket or unit. The main purpose of this component is to provide a surface for microorganisms to attach to, thereby forming a biofilm. This component may comprise any suitable material. The material may have, or may have been treated or modified (e.g. being machined or coated) to produce, a rough or porous surface. Alternatively, the additional component may be entirely porous, comprising any suitable porous material, such as a sponge material, a protein, a scaffold matrix or a mesh.

The additional component can be positioned anywhere within the unit of the device. In some embodiments the additional component is in contact with the inside of one or both of the outer layers of the device. The component may cover the entire inside surface of the layers or only a portion thereof.

The additional component is suitably at least translucent, and typically transparent. In some embodiments, the additional component can be coated on one or both sides with a biological support. In such an arrangement, the microorganisms attach to the biological support, rather than to the surface of the additional component, therefore the additional component does not need to be porous or have a rough or porous surface; the additional component can be made of any material that can support the coating.

Biological Support

In an embodiment, the device of the invention further comprises a biological support located within the pocket formed by the first and second layers. The biological support is a material that provides a physical structure or a chemical interface for the photosynthetic microorganisms to attach to. The biological support may be modified to enable attachment of the microorganism.

The biological support optionally comprises a coating, such as a protein coating, and/or a chemical coating. Typically, the biological support coating has a thickness no less than 0.1 nm, suitably 0.5 nm, optionally not less than about 50 nm. In an embodiment, the biological support coating has a thickness of 1 nm. The biological support may have a thickness of up to 30 microns, and even as much as 50 microns in some embodiments of the invention.

Suitably, the biological support is at least translucent, and typically transparent.

As mentioned above, light can reach the device from a single direction or from multiple directions. The photosynthetic microorganisms located within the device may be drawn (e.g. via phototaxis) to the side of the device nearest to the primary light source and may attach to the inside surface of the side of the device, forming a biofilm. However, this may not be desirable, as the formation of a biofilm on the inside surface of the part of the device closest to the primary light source may prevent light from reaching other parts of the device. The presence of the biological support component of the device allows the location of microbial growth within the device to be controlled and facilitates growth in the desired locations. The biological support component can be used to encourage biofilm formation in regions of the device that will allow for optimum passage of light through the device, and hence facilitate maximum photosynthetic efficiency of the photosynthetic microorganisms contained within the device, and hence to maximise the efficiency of generation and regeneration of biomass. The position of the biological support within the pocket can vary according to the specific composition and arrangement of the device. For example, the biological support can be located close to or in contact with the internal surface of either or both of the first and second layers. It can partially or entirely cover the inside surface of either or both of the layers. Alternatively, the biological support can be located centrally within the pocket (i.e. not in contact with the inner surface of the first or second layers). In a typical embodiment, if light reaches the device primarily from a single direction, the biological support is used to promote growth and biofilm formation on the opposite side, furthest away from the main light source.

In embodiments of the invention that comprise an additional component polymer or porous component as discussed above, the additional component may be partially or entirely coated by the biological support.

Microorganisms

It is envisioned that the microorganism contained within the unit of the device is capable of photosynthesis. Any microorganism that is capable of photosynthesis is referred to herein as a photosynthetic microorganism. In a suitable embodiment, the photosynthetic microorganism is selected from micro-algae (such as green, blue-green, golden and red algae), phytoplankton, dinoflagellates, diatoms, bacteria and cyanobacteria, such as *Spirulina* sp. The microorganism may be a wild-type or genetically-modified strain. A single device according to embodiments of the invention may comprise one or more different types of microorganisms.

Typically, at least one microorganism is a *Haematococcus* sp., *Haematococcus pluvialis*, *Chlorella* sp., *Chlorella autotraphica*, *Chlorella vulgaris*, *Scenedesmus* sp., *Synechococcus* sp., *Synechococcus elongatus*, *Synechocystis* sp., *Arthrospira* sp., *Arthrospira platensis*, *Arthrospira maxima*, *Spirulina* sp., *Chlamydomonas* sp., *Chlamydomonas reinhardtii*, *Geitlerinema* sp., *Lyngbya* sp., *Chroococcidiopsis* sp., *Calothrix* sp., *Cyanothece* sp., *Oscillatoria* sp., *Gloeothece* sp., *Microcoleus* sp., *Microcystis* sp., *Nostoc* sp., *Anabaena* sp.

*Dunaliella salina* and *Synechococcus marinus* are typical microorganisms in embodiments where the liquid media passing through the channels in the device comprises salt water.

Coatings to Prevent Microbial Growth and Attachment

In order to control where microorganisms adhere and grow to form a biofilm within the device, and where they do not grow, any component of the device described herein, or a portion thereof, can be coated with a hydrophobic, hydrophilic or antimicrobial coating or can be machined or otherwise transformed physically or chemically to have hydrophobic, hydrophilic or antimicrobial characteristics. As used in this context, the term "portion" means a sufficient amount of the component to provide said component with hydrophobic, hydrophilic or antimicrobial characteristics.

The antimicrobial agent may be a physical modification, such as a rough surface, or a chemical modification, such as a coating.

Suitable anti-microbial agents include organosilanes, silver, silver alloys, copper and copper alloys.

Typical hydrophobic coatings include Teflon™, PTFE, poly(methyl methacrylate) (PMMA), graphene and carbon nanotubes. As the skilled person will be aware, it is also possible to create "super hydrophobic" surfaces, for example using fluorocarbons.

Hydrophilic coatings can also prevent microbial attachment and biofilm formation. Suitably, such hydrophilic coatings are based on highly hydrated zwitterions, such as glycine, betaine and sulfobetaine.

These coatings prevent microorganisms located within the unit from adsorbing to the internal surfaces of the component. In this way, it is possible to control where microbial growth and attachment occurs within the device. This is beneficial for optimising the passage of light through the device, which results in optimum photosynthesis by photosynthetic microorganisms located within the device, and hence optimum generation of biomass. Controlling the location of microbial growth and biomass formation in this way also aids and facilitates optimum harvesting of biomass from the device.

For example, it may be desirable to prevent microorganisms from attaching to the inside of the membrane layer and forming a biofilm, because the formation of a biofilm can prevent light from reaching the interior of the pocket of the device. This may be particularly important in embodiments where the membrane layer is positioned on the side of the device that is nearest to the light source. Therefore, in a typical embodiment of the invention, at least a portion of the inside of the membrane layer (i.e. the side of the membrane layer that is inside the pocket formed by the two outer layers) is coated with a hydrophobic, hydrophilic or antimicrobial coating or can be machined or otherwise transformed physically or chemically to have hydrophobic, hydrophilic or antimicrobial characteristics, in order to prevent microbial growth and attachment.

In other suitable embodiments, the inside surface of the second layer can be coated with a hydrophobic, hydrophilic or antimicrobial coating or can be machined or otherwise transformed physically or chemically to have hydrophobic, hydrophilic or antimicrobial characteristics.

In instances where light reaches the device from primarily one direction, it is typical to encourage microbial growth on the interior surface of the outer layer that is located furthest away from the main light source.

Fluid Conduits

One or more fluid conduits suitable as channels for directing liquid media and water, having an inlet (1) and an outlet (2), are arranged within the unit to optimise fluid flow rates through the units. In a particular embodiment, they may comprise liquid media conduits. Suitable, but non-limiting, fluid velocity rates are not less than about 1 ml/min, typically 50 ml/min, and optionally 200 ml/min. Depending upon the size of the system and the configuration flow rates up to 30 L/min, suitably 10 L/min and around 1 L/min are also possible. Fluid velocity can be varied according to the photosynthetic activity of the photosynthetic microorganisms contained within the device at a given time, which may depend on external factors, such as temperature and light intensity.

Additionally, fluid flow rate can vary with the width and thickness of the fluid channels, as well as the device's mounting orientation.

Maintaining a constant low rate also helps to prevent microorganisms attaching to the membrane layers and/or to additional components not specifically intended to support biofilm formation. The fluid flow rate can dynamically change over very small and/or large time periods (seconds, minutes, hours, days).

In a typical embodiment the one or more fluid conduits are configured to direct the flow and facilitate exchange of liquid media between the unit and a liquid media source.

This is suitably achieved by control structures, which are positioned within the unit and form barriers to the passage of liquid media through the unit, thereby forming defined channels. The control structures can be made of any suitable translucent, or more typically transparent, material. Alternatively or additionally, control structures may be formed by bonding discrete regions of the two outer layers. This bonding can be achieved using heat-pressing or a glue interface. The control structures/bonded regions increase the structural integrity of the device, facilitate liquid media flow, increase the control of the device thickness and shape when the unit is inflated by liquid pressure.

Alternatively or additionally, control structures may be formed by bonding discrete internal regions of the two outer layers to structural components. This bonding can be achieved using heat-pressing or a glue interface. The control structures/structural component-bonded regions increase the structural integrity of the device, facilitate liquid media flow, increase the control of the device volume, thickness and shape when the unit is inflated by liquid pressure.

The arrangement of the fluid conduits creates spaces where liquid media flow is optimised. Also fluid conduits can distribute the liquid media homogeneously throughout the unit, maintaining a similar liquid media flow rate. In a suitable embodiment, the one or more fluid conduits are configured to allow removal of microorganisms/biomass from the unit, and/or allow the liquid media with the microorganisms to flow through an illuminated path. The optimised configuration of the fluid conduits also facilitates temperature control within the device. Specific arrangements of channels are exemplified in detail below.

The device (or module comprising multiple units) is connected via one or more inlets to a liquid media supply.

The device can be connected to the liquid media supply using additional attachment components or adjoining mechanisms (e.g. rigid fixing, flexible fixing, clamped, pressure fitting, connected by conduit).

In a separate embodiment of the invention, the minimum requirement is for the device to comprise a single fluid conduit having a single opening that functions as both an inlet and an outlet.

A second aspect of the invention is directed to a photo-bioreactor module. The photo-bioreactor module comprises a plurality of devices as defined above.

In a typical embodiment of this aspect of the invention, each individual unit is connected to one or more devices via the liquid media channel inlet/outlet. Multiple devices can be connected to each other liquid media channel inlet/outlet using additional attachment components or adjoining mechanisms (e.g. rigid fixing, flexible fixing, clamped, pressure fitting, connected by conduit).

Single and/or Multiple devices can be connected to the liquid media supply using additional attachment components or adjoining mechanisms (e.g. rigid fixing, flexible fixing, clamped, pressure fitting, connected by conduit).

Suitably, the module is fabricated as a single modular unit. Multiple photo-bioreactor modules can be connected to each other liquid media channel inlet/outlet using additional attachment components or adjoining mechanisms (e.g. rigid fixing, flexible fixing, clamped, pressure fitting, connected by conduit).

Single and/or Multiple modular units can be connected to the liquid media supply using additional attachment components or adjoining mechanisms (e.g. rigid fixing, flexible fixing, clamped, pressure fitting, connected by conduit).

Artificial Light Source

The device of the invention can receive light from external natural or artificial sources. Alternatively, in order to increase the amount of light available to the photosynthetic microorganisms contained within the pocket, an artificial light source can be positioned within the device.

Typically, the artificial light source is selected from a light-emitting diode (LED) or an organic light-emitting diode (OLED), or a fibre optic or optic embedded within the device and connected to an external natural or artificial light source.

Suitably, the artificial light source is designed and/or controlled to emit specific wavelengths of electromagnetic radiations (Light) following the photosynthetically active radiations (PAR) needs of the photosynthetic microorganisms contained within the device.

In a suitable embodiment that is illustrated in FIG. 33, the artificial light source is partially or fully embedded within one or more translucent or transparent control structures/structural components located between the first and second layers.

Additionally, an optic and/or fibre optic cable, connected to an external light source, can be partially or fully embedded within one or more translucent or transparent control structures/structural components located between the first and second layers.

Shape and Dimensions

The following features can apply to devices comprising a single unit according to embodiments of the invention or to modules comprising multiple units, according to other embodiments.

When the unit is inflated by liquid media pressure the shape can be similar to a squashed tube, because of this the optimal thickness and/or volume can vary.

Suitably, the overall thickness, when inflated by liquid media pressure, of the device, unit or module of the invention is as thin as possible, to enable light to travel all the way through the device, maximising the photosynthetic capacity and efficacy of biomass generation of the device. Typically, the thickness is no less than 2 mm, suitably 5 mm, typically 10 mm. The thickness is typically no more than 100 mm, suitably 60 mm, typically 35 mm.

The shape of the unit can be controlled to be a flat or nearly flat shape (with a rectangular cross-section rather than a tubular cross-section) by using external containment structures such as meshes or thin solid materials, and/or by stretching the unit from the opposite bonded regions and/or folded regions and/or edges of the unit.

The depth and width of the device or modular photo-bioreactor is also important for controlling the temperature within the device, because these affect the amount of liquid media that can be contained within the device. A device that has a greater depth and width will be able to accommodate a greater number of fluid conduits and a greater volume of liquid media.

The length and width of the fluid conduits varies in respect to each application and unit shape, therefore it can be of any reasonable length and width. As an example, the length of a fluid conduit inside a linear unit is no less than 5 cm, and no more than 10 meters. Suitably, the width of a fluid conduit inside a unit is no less than 1 cm, typically 3 cm, and no more than 20 cm, suitably 10 cm.

The 2-dimensional or 3-dimensional shape of the device or module is not restricted; it can be any convenient shape, such as a rectangular shape or any shape having a constant width, or any shape that narrows at the top and bottom around the inlet and outlet portions, or a leaf shape, a circular shape, an elliptical shape, cross-shaped, square-shaped, streamlined or star-shaped. Examples of suitable shapes are discussed in more detail below.

A third aspect of the invention is directed to a method of using of a device or photo-bioreactor module as defined herein to generate biomass.

In addition, the device may also be used to generate oxygen and/or to remove environmental pollutant gases, such as carbon dioxide, from the atmosphere.

Mechanisms of Function

Due to the membrane layers of the unit, gas exchange occurs through the membranes between the liquid media comprised within the unit and the atmosphere outside the unit. As shown in FIG. 34, any species of permeant gas can be exchanged through the membrane in either direction, that is, gases can permeate from the liquid media to the outside atmosphere (5) or from the outside atmosphere to the liquid media (6). The gas permeation rate will change in respect to the partial pressure difference of the permeant gas between the inside of the unit and in the outside of the unit. In a suitable embodiment of this invention, carbon dioxide is consumed by the microorganisms in the liquid media inside the device, which decreases the carbon dioxide concentration in the liquid media. New carbon dioxide permeates through the membrane from the outside air inside the device due to the resultant pressure differential between the inside and the outside of the device. Furthermore, in a typical embodiment, the oxygen produced by the microorganisms permeates through the membrane from the liquid media inside the device to the outside of the device.

This membrane driven gas transfer advantageously allows for a significant decrease in costs related to aeration which, instead of being performed through more complicated and expensive gas delivery systems, is performed by a passive membrane-driven gas permeation without additional energy input. It is known that carbon dioxide is a fundamental component of photosynthesis and, if high light levels are present and carbon dioxide is efficiently delivered to the microorganisms inside the liquid media, sustaining their need for the gas, the biomass generation rate can increase dramatically. On the other hand the oxygen produced by the microorganisms is usually dissolved in the liquid medium, increasing the oxygen concentration in the device. It is known that high levels of dissolved oxygen in the liquid medium slows down the photosynthetic process, therefore slowing down the biomass generation rate.

The efficient depletion of oxygen from the liquid media inside standard photo-bioreactors can be both difficult and costly to achieve mainly because the dissolved oxygen needs to be driven from the liquid media to the outside of the photo-bioreactor through air vents mostly by utilising bubbling in the liquid media.

In most standard photo-bioreactors the liquid media flows inside non-membrane conduits for a prolonged time before reaching an air vent, bubbling area, aeration inlet and/or water tank. Thus, the liquid media can have very high levels of dissolved oxygen and very low levels of carbon dioxide, causing a severe decrease of biomass generation rate. Using a gas permeable photo-bioreactor, gas exchanges between the liquid media inside the device and the outside of the device can occur continuously during flow.

The advantages of performing this membrane driven gas transfer in photo-bioreactor technologies are increased adaptability, reduced costs and increasing the quality of the microbial culture in the liquid media by the efficient removal of oxygen.

Auxiliary System

The device may be connected to an auxiliary system. Depending on the application of the device, the auxiliary system can be of any degree of complexity and composed by any kind of auxiliary components.

In a suitable embodiment of this invention, the device is connected to an auxiliary system mainly composed by conduits, water tanks, pumps, valves, biomass-separators, artificial lighting systems (especially if natural light is not present), water temperature control systems, sensors and computers.

The conduits and reservoirs (water tanks) can be of any type and of any suitable material.

The pumps can also be of any type, typically the pumps are peristaltic pumps which can reduce the contamination risk of the liquid media and the breakage of the cells of the microorganisms used due to the use of a peristaltic tube which is the only component in contact with the liquid media.

Biomass-separators can be of any type known to the skilled person; suitably the biomass-separator is a centrifuge type bio-separator, a filtering system comprising small-aperture meshes, and/or a sedimentation device, and/or clarification process.

The water temperature control can be of any type known to the skilled person; typically it comprises a heating component which is suitably installed around parts of the conduits and/or on the water tank. The heating components can be of any type, and suitably can comprise heat-exchange mechanisms.

The artificial lighting system can use any artificial light source types known to the skilled person, suitably the lighting system is comprises LEDs, typically the artificial light source is designed and/or controlled to emit specific wavelengths of electromagnetic radiation (Light) corresponding to the photosynthetically active radiation (PAR) needs of any photosynthetic microorganisms contained within the device.

Suitable sensors and computers are described below.

FIG. 35 shows a suitable system of one embodiment of the invention (90) comprising multiple photobioreactor units (105). The liquid media comprising a photosynthetic microorganism in a reservoir (91) is conveyed by a pump (92) into a rectangular photobioreactor unit (105) through the inlet (1). The liquid media passes along a tortuous path through the unit (105) where light from an artificial light source (93) or natural light source reaches the microorganisms in the liquid media stimulating photosynthesis, meanwhile gas transfer between the liquid media in the unit (105) and the outside air occurs through the membrane layers of the unit substantially as shown, for example, in FIG. 34. The liquid leaves the unit through the outlet (2) and reaches a 3-way valve (94) which directs the liquid media back into the reservoir (91), closing the circuit. Sensors (95) in the reservoir (91) measure the values of microorganisms culturing parameters and send outputs to the computers which then control operations of the auxiliary system's components, such as pumps, valves, artificial light systems, temperature control systems, biomass-separators.

When the biomass concentration in the liquid media reaches the desired level, the 3-way valve (94) directs the flow into the biomass-separator (96) which separates the biomass from the liquid media, the isolated biomass proceeds into a receptacle (97) for additional processing, while the liquid media is directed back into the reservoir (91). This action of directing the flow into the biomass-separator can be performed periodically and for a predetermined period of time before the valve (94) changes the flow path into the reservoir (91) again. This timing can be optimised with respect to each application, the microorganism used, the surrounding environment and location of the device.

Nutrients can be periodically inserted (98) in the system directly into the reservoir (91). Water and/or microorganisms in liquid media, or cleaning fluid, can be similarly introduced.

All sorts of other system components can be utilised, as example a controllable pressure valve or pressure regulator (99) can be placed in the system, in this example the pressure valve can control the volumetric change of the unit through the effects of changes in the liquid pressure. Some valves (102) can control the flow rate into the units.

Supplementary air and/or air enriched with carbon dioxide and/or other gases can optionally be introduced (101) in the main conduit if required. Air vents can be installed in the conduits to remove air that can accidentally enters the hydraulic system, for example during installation of the system, and are typically located in the highest location of the system to facilitate the expulsion of undesirable air.

A cleaning procedure can be actuated to clean and/or sterilise the unit and/or the conduits and/or the water tank and/or all the auxiliary system. A "cleaning liquid" can be made of any compound the skilled person will know. It may comprise ethanol, water, salty water, detergents, bleach, surfactants, alkali or any other suitable cleaning composition. The cleaning liquid can enter the system through specific conduits in any point of the system and can exit at any point of the system to permit cleaning in specific locations only, if desired, instead of cleaning the entire system.

Holding and Installation Solutions

The device or devices of this invention can be installed in all orientations and positions following its intended application and/or its installation location's environmental characteristics. The units of the device can have reinforced borders, located adjacent to the seals and pockets defined therein, suitably located at the external bonding areas. Reinforced panels are suitable for fixing to an external mounting structure. In a preferred embodiment the unit's borders are reinforced with multiple fixing points enabling attachment to an external mounting structure, such as a frame or support. The reinforced borders may also serve to strengthen the structure of the unit and potentially control its thickness and/or volume when inflated by liquid media within.

If installed in a vertical, substantially vertical and/or substantially oblique position, the device or devices can be suspended from the mounting structure through either the inlet or the outlet conduit, the reinforced borders of the unit, or through a reinforced suspension structure. The device or devices can lie on a bed which can provide a mounting interface between the ground and the device, this is well suited for horizontal, substantially horizontal and/or substantially oblique positioning (such as on the pitched roof of a building). The support bed can be comprised of a mirror or other light reflective material in order to enhance collection of light which passes through the units of the device.

In embodiments where the unit or units are made of single folded membrane layer (FIG. 32a, 32b) the folded edge (88) can function as a fixing point to a mounting structure, and the folded edge can be clamped or reinforced.

Additional Component Layer

In another embodiment of this invention, as shown in FIGS. 5 to 9, the additional component (15,16), may be placed inside the unit, in contact with one or more of the outer membrane layers, or it can be in the form of a third layer (89) which can be fixed in place by bonding it through a glue interface (82) to the two outer membrane layers as shown in FIGS. 33a, and 33b. Optionally structural components (83) can be bonded in between the additional component layer and the outer membrane layers as shown in FIG. 33b. The additional component layer (89) can divide a single fluid conduit in two, in a different orientation than the one created by control structures (27, 37, 47), described above.

Extruded Version

In an embodiment, the unit can be made of a single sheet of gas permeable membrane that is extruded in a tube-like shape (FIG. 38). This embodiment removes the need to bond the ends because it is already closed on two sides, thereby defining the pocket. Bonding between the two sides of the same extruded layer can be used to create control structures as described above. Optionally, the edges (88) can function as a fixing point to a mounting structure, the folded edge can be clamped or reinforced.

Non-Membrane Options

In another embodiment of this invention (FIG. 39), the outer layers of the unit comprise one membrane layer (11) and one non-membrane layer (18). The non-membrane layer (18) can be made of any material, suitably a flexible or inflexible translucent material, optionally a transparent or optically clear material such as a glass. The non-membrane layer (18) is introduced when the gas permeation through the membrane layer (11) is sufficiently high to provide the ideal gas transfer between the liquid media and the atmosphere outside the unit (10). This embodiment can include additional components and configurations as described in any one of the other embodiments above.

Applications

The device of this invention can be utilised for many applications. The applications can be of any kind where biomass production, carbon dioxide sequestration, oxygen production, the sequestration of nitrogen oxides or other gases is needed, or where waste water treatment is needed, or even for aesthetic applications. The device can be used indoors and/or outdoors.

Suitable applications for the device of this invention can be any indoor and/or outdoor architectural applications including, but not limited to, being part of a building façade, roofs, sun-canopies, sun shades, windows, and/or indoor ceilings, indoor walls, or indoor floors. In these applications, produced oxygen can be used inside the building and/or the carbon dioxide can be absorbed from inside and/or outside the building.

Suitable applications for the device of this invention can be together with any lighting systems and/or lighting fixtures, including, but not limited to, interior lighting systems such as ceiling, ground, wall, desk, suspended, technical, decorative, outdoor, street lighting, or advertising lighting fixtures.

In such applications, the artificial light source provided from the lighting system can provide most of the light needed by the microorganisms to photosynthesise, and the produced oxygen can be used inside the building and/or the carbon dioxide can be absorbed from inside and/or outside the building.

Additional suitable applications for the device of this invention can be intensive biomass production applications, including, but not limited to, outdoor intensive biomass production plants using mostly natural light sources, indoor intensive biomass production plants using artificial light sources and/or natural light sources, such as in greenhouses.

Further suitable applications for the device of this invention can be together with infrastructures, including, but not limited to, urban infrastructures, motorways, bridges, industrial infrastructures, cooling towers, highways, underground infrastructures, traffic sound barriers, silos, water towers, or hangars.

Other suitable applications for the device of this invention can be in combination with waste treatment plants, including, but not limited to, waste water treatment plants, municipal waste water treatment plants, sewage anaerobic digestion treatments, manure anaerobic digestion treatments, anaerobic digesters or incinerators.

The device of this invention can remove pollutants and/or nutrients (such as nitrates and phosphates) directly from waste water streams which can be diverted inside the units. This is favourable in waste water treatment applications and building/industrial applications where a partial and/or pre-treatment of water is demanded. Water containing contaminants that are toxic to the microorganisms within the device of the invention should in such embodiments be treated to remove these contaminants prior to being introduced into the device.

The device of this invention can be installed next to any kind of industrial processes and/or agricultural processes and/or farming processes and/or intensive farming processes (intensive fish farming) and/or manufacture processes and/or refinery processes and/or energy production processes where the exchange of any kind of compounds and gases can occur between the device (with the auxiliary system) and this processes.

Continuous Harvest

An advantage of some embodiments of the invention is that biomass can be generated continuously within the unit and can be harvested on a continuous basis.

Biomass accumulates in the liquid media within the unit, either in regions of biofilm that form on the surface of components of the device, including the biological support component, the additional component or on the inner surfaces of the two outer layers, as described in detail above. The biomass can be harvested directly from the liquid media, and optionally also with chemical treatment to facilitate biomass detachment from the inside of the device. In order to purge the device and release biomass, liquid media enters the device via the one or more inlets, passes through the one or more channels and exits the device, together with biomass that is carried in the flow, via the one or more outlets. The outlet can be connected to a suitable receptacle for receiving the harvested biomass.

In embodiments where a biofilm is intentionally grown within the device, the biofilm functions to provide a fixed active photosynthetic microbial surface, which prevents some of the microorganisms from being washed away when the device is flushed through. This facilitates rapid generation of biomass and allows for continuous harvesting of biomass generated in the device. This enables the device to regenerate/replenish biomass quickly, because the microorganisms that remain within the device can continuously generate biomass via photosynthesis (provided that the light conditions allow photosynthesis). Furthermore, new/additional microorganisms do not have to be introduced into the pocket after biomass has been harvested in order for more biomass to be generated.

Batch Harvest

Alternatively, biomass can be harvested intermittently, on a batch basis. For example, biomass can be harvested from the device frequently, on an hourly, daily or weekly basis.

Sensors

Embodiments and/or the auxiliary system of the invention can include embedded sensors which can be used, for example, to monitor chemical concentrations such as carbon dioxide concentrations and/or oxygen concentrations in liquid and/or gas; and/or to monitor temperature and other environmental and biological parameters, such as toxicity levels and/or to monitor the biomass concentration in the liquid media.

Sensors can be embedded entirely or partially in the device, in the water tank of the auxiliary system, and/or in control structures and/or be attached to the inside or outside of external layers or on surface of internal additional components.

Sensors can permit the monitoring of the environment inside the pocket of the unit of the device, in order to enable control of parameters including, but not limited to, liquid media flow rate, liquid media quality, nutrient levels, temperature, biomass extraction rate and lighting intensity. The purpose of this control is to optimise the photosynthetic efficiency of the photosynthetic microorganisms contained within the device, and hence to optimise the efficiency of generation of biomass.

The device of the invention is exemplified by, but in no way limited to, the following arrangements.

Two Membrane Layers

A device according to a specific embodiment of the invention is shown in FIG. 1. The device comprises a unit (10) that has two membrane layers (11, 12), an inner space (13) defined by the membrane layers, an inlet (1) and outlet (2). The two membrane layers (11, 12) can have the same or different compositions. There can be microbial growth on the inside of one, both or neither of the membranes.

In a suitable embodiment, a biological support (15) is present on the inside of one or both layers. The biological support facilitates microbiological growth and the formation of a biofilm. An arrangement wherein a biological support is present on the inside of both membrane layers (11, 12), is shown in FIG. 3, while FIG. 4 shows an arrangement with a biological support present on the inside of one membrane layer.

Another embodiment of the device comprises a unit (10) comprising two membranes (11,12) and can also comprise an additional component (14), as defined above, which may be located in the pocket (13) formed by the two layers. Such an arrangement is shown in FIG. 2. It may be desirable for the microorganisms to attach to the additional component rather than to the internal surfaces of the membrane layers (11, 12). The fluid flow rate can be high enough to prevent microbiological growth on the membrane layers. However, the inside surface of the membrane layers (11, 12), or a portion thereof, can be hydrophobic or can be coated with a hydrophobic, hydrophilic or antimicrobial coating or can be machined or otherwise transformed physically or chemically to have hydrophobic, or antimicrobial characteristics.

The additional component (14) can optionally be coated on one or both sides with a biological support (15), as illustrated in FIGS. 5 and 6. In this embodiment, the microorganisms attach to the biological support, rather than to the surface of the additional component, therefore the additional component does not need to be porous or have a rough or porous surface.

FIGS. 7, 8 and 9 illustrate a device comprising a unit (10) having first and second membrane layers (11, 12) and an additional component (16) located in the pocket formed by the two layers. In this embodiment, the additional component (16) is made from a porous material and may be attached to either or both membrane layers, or may be located within the pocket (13).

One Membrane Layer and One Non-Membrane Layer

A device comprising a unit (10) according to some embodiments of the invention can have one membrane layer (11) and one non-membrane layer (18), as described above. Such an embodiment is illustrated in FIG. 39. In this embodiment, the non-membrane layer may be modified or treated to produce a rough surface to promote attachment of microorganisms and the formation of a biofilm.

If the device is illuminated primarily from a single direction, the membrane layer may be located on the side of the device nearest to the primary light source and the non-membrane layer may be located on the side of the device furthest away from the primary light source. Alternatively, the non-membrane layer may be located on the side of the device nearest to the primary light source and the membrane layer may be located on the side of the device furthest away the light source.

As described above in relation to the two membrane arrangement, a device comprising a membrane layer and a non-membrane layer can also comprise an additional component, which may be coated, as defined above, which may be located in the pocket (13) formed by the two layers (11, 12).

Configuration of the Fluid Conduits

A simple streamlined version of an embodiment of the invention, having one fluid conduit with an inlet (1) and an outlet (2) located on opposite sides, is illustrated in FIG. 10. In this front-view representation of the device (20), liquid media flows in via the inlet (1) at the top, flows through the space within the pocket (23) and exits via the outlet (2) at the bottom on the device.

A simple streamlined version of an embodiment of the invention, having two fluid conduits and a single control structure is illustrated in FIG. 11. In this front-view representation of the device a unit (20) is provided, the central portion (27) represents a region where the two outer layers are bonded together, and/or where a control structure is located. Fluid flows in via the inlet (1) at the top and is divided into two channels (23), to the left and right of the bonded region/control structure. Liquid media from both channels (23) exits via the outlet (2) at the bottom of the device.

A streamlined version of an embodiment of the invention, having multiple flow control structures (27) is illustrated in FIG. 12. In this front-view representation of the device (20), the central portion has both linear and streamlined flow control structures. fluid flows in via the inlet (1) at the top and is split into four channels (23). Fluid from all channels exits via the outlet (2) at the bottom of the device.

A streamlined version of an embodiment of the invention (20), having multiple dimple-like circular flow structures (28) is shown in FIG. 13. In this front-view representation, the pocket comprises an array of multiple flow control structures (28). These structures may be circular or any other convenient shape. The control structures create turbulence as well as multiple different pathways that liquid media can flow through. As with the previous examples, in this arrangement the inlet (1) is located at the top of the representation and the outlet (2) is at the bottom.

FIG. 14 shows an arrangement (20) that is designed to increase the surface area of the device that is exposed to light in order to increase the photosynthetic capacity and efficacy of biomass generation of the device. In this example there are multiple protruding portions (29), each comprising flow control structures (27) as described above.

A different version of the device comprising a unit (30) as shown in FIG. 15. In this representation of a device, the inlet (1) and the outlet (2) are located adjacent to each other, on the same side of the device. There is a linear flow control structure, which forms a single channel (33) within the unit and creates an optimised flow path. The flow is directed down through the device from the inlet (1) at the top and then loops back, to exit the device via the outlet (2), which is also located at the top of the device.

FIG. 16 also shows a version of the device in which the inlet and the outlet are located adjacent to each other, on the same side of the device. In this front-view representation of the device, the central portion has both linear and streamlined flow control structures (37), which create two channels (33). The flow is directed from the inlet (1) at the top, down through the two channels and then loops back, to exit the device via the outlet (2), which is also located at the top of the device.

FIG. 17 shows a typical configuration of the device comprising a unit (40) of the invention. The device is linear (substantially similar to a rounded parallel piped or squashed/elliptical tube shape). This shape is simple to manufacture and is particularly suitable for arranging with multiple other devices in a modular manner. In this representation, the width of the device is reduced at the top and bottom, around the inlet (1) and outlet (2). However, this does not need to be the case; the width can be consistent along the length of the device, or the width can vary (increase or decrease) along the length. The length can also be varied according to the required application of the device. In this representation, there is one fluid conduit with an inlet (1) and an outlet (2) located on opposite sides.

FIG. 18 shows a device comprising a unit (40) that is similar to that described above in FIG. 17, but the introduction of a linear control structure (47) in the central portion of the device creates bifurcated channels (43). Fluid flows in via the inlet (1) at the top and is diverted along the two channels (43). Fluid from both channels exits via the outlet (2) at the bottom on the device.

FIG. 19 shows a device comprising a unit (40) that is similar to that described above in FIG. 20, but the introduction of multiple flow control structures (48) (which may be round or any other convenient shape) create multiple different pathways that liquid media can flow through. In the arrangement shown here the inlet (1) is located at the top of the device and the outlet (2) is at the bottom.

FIG. 20 shows a version of the device comprising a unit (50) having four branches, with inlets (1) and outlets (2). The inlets and outlets can be positioned at any of the four positions shown in this representation. At the centre of the four branches, there is a control structure (57) to regulate flow through the device and its structure. This arrangement (50) can be used to join multiple modules, units or devices together, or it can be used by itself or in an array with other devices of the same shape.

A different arrangement having multiple protruding portions (49), similar to the arrangement shown in the streamlined device in FIG. 14, is shown in FIG. 21. The inlet is at the top of the device (1) and the outlet (2) is at the bottom. There are multiple channels through which liquid media flows within the device. This arrangement is designed to increase the surface area of the device that is exposed to light in order to increase the photosynthetic capacity and efficacy of biomass generation of the device.

FIG. 22 shows a linear device comprising a unit (60) with a single channel created by a linear flow control structure (67). Both the inlet (1) and the outlet (2) are located on the same side of the device (i.e. at the top of the device in this illustration). The linear flow control structure in the centre of the device forms a single channel within the device. The flow is directed down through the device from the inlet at the top and then loops back, to exit the device via the outlet, which is also located at the top of the device.

FIG. 23a shows a square-like rectangular device comprising a unit (70) with a single channel (73) created by control structures (77). The inlet (1) is at the top of the device and the outlet (2) is at the bottom. In this arrangement the fluid can flow by gravity force and it is optimised to fill panel-like areas with little requirement for energy inputs for pumping.

Similar to FIG. 23a, FIG. 23b shows a square-like device comprising a unit (70) with a single channel created by control structures (77). Both the inlet and the outlet are located on the same side of the device (i.e. at the top of the device in this illustration). The linear flow control structures forms a single channel (73) within the device. The flow is directed down through the device from the inlet at the top and then loops back, to exit the device via the outlet, which is also located at the top of the device.

FIGS. 24 to 26 show photo-bioreactor module arrangements comprising multiple individual devices, in accordance with the second aspect of the invention. Such modular arrays can be used to fill large spaces. By using multiple identical devices in a modular manner bio-reactor maintenance costs can be minimised. It is within the scope of the invention for the photo-bioreactor module to comprise multiple individual devices that are identical to each other or non-identical.

FIG. 24 shows a module comprising streamlined devices. These could, for example, be any of the devices (20) shown in FIGS. 10-16.

FIG. 25 shows a module comprising linear devices. These could, for example, be any of the devices (40) shown in FIGS. 17-19.

FIG. 26 is an example of a modular array device that comprises multiple units (70) that are designed to fill a squared area. Devices according to the invention can be configured in various embodiments to fill a variety of different shapes, as required.

FIG. 27a,b,c shows the cut section through a representation of some embodiments of the invention and is included to aid understanding of the other drawings provided herein.

FIG. 30 shows a cross-sectional view (Section D in FIG. 27c) of a device (80) according to an embodiment of the invention having two control structures located between the first and second layers. These structures, which can be made from any suitable translucent (or typically transparent) material, are positioned within the pocket to control the passage of liquid media through the device and provide structural support to the device.

FIG. 28a shows a cut-sectional view (Section B of FIG. 27a) of a unit (80) according to an embodiment of the invention having first and second membrane layers (81, 84) bonded together through a glue interface (82).

FIG. 28b shows a cut-sectional view (Section B of FIG. 27a) of a unit (80) according to an embodiment of the invention having first and second membrane layers (81, 84) with a structural component (83) in between where the membranes are bonded through a glue interface (82).

FIG. 29a shows a cut-sectional view (Section D of FIG. 27c) of a unit (80) according to an embodiment of the invention having a first and second membrane layers (81, 84) bonded together through a glue interface (82). The central bonding (85) is a control structure which creates two fluid conduits.

FIG. 29b shows a cut-sectional view (Section D of FIG. 27c) of a unit according to an embodiment of the invention having a first and second membrane layers (81, 84) with a structural component (83) in between where the membranes are bonded through a glue interface (82). The central bonding (85) is a control structure which creates two fluid conduits.

FIG. 30 shows a cut-sectional view (Section D of FIG. 27c) of a device (80) according to an embodiment of the invention representing a mixed composition of bonding techniques to create bonds (82) between the membrane layers.

FIG. 31 shows a cut-sectional view (Section D of FIG. 27c) of a device (80) according to an embodiment of the invention, wherein an artificial light-source (87) is embedded inside the bioreactor and specifically inside a control structure (86) (indicated by single and dashed line hatching) located between the first and second membrane layers.

FIG. 32a shows a cut-sectional view (Section C of FIG. 27b) of a device according to an embodiment of the invention, wherein the unit is composed of a single tube-like shaped membrane layer (81) extrusion which is bonded to itself (82) at one end through a glue interface.

FIG. 32b shows a cut-sectional view (Section C of FIG. 27b) of a device (80) according to FIG. 32a, having a structural component (83) in between where the membrane (81) is bonded to itself (82) through a glue interface.

FIG. 33a shows a cut-sectional view of a unit (80) according to an embodiment of the invention having first and second membrane layers (81, 84), wherein an additional component (89) is located inside the unit formed by the two membrane layers.

FIG. 33b shows a cut-sectional view of a unit (80) according to FIG. 33a, having a structural component (83) in between where the membranes (81, 84) are bonded through a glue interface (82).

FIG. 34 shows a cut-sectional view of a unit according to an embodiment of the invention having first and second membrane layers (3,4), and representing the optional directions of the gas permeation through the membrane layers, either outwards (5) or inwards (6).

Generating and Harvesting Biomass

FIG. 36 is an illustration of a suitable process cycle (150) of generating and harvesting biomass (either on a continuous or batch basis) using the device of the invention. (A) shows the initial state, when the device is installed and is empty. (B) shows the initiation phase, when the device is filled with liquid media containing photosynthetic microorganisms. At this stage the biomass is generated within the device until it reaches the desired biomass density levels in the liquid media, represented by stage (C). In a more preferred embodiment of this invention, this system cycle is a continuous system cycle, after stage (C) the liquid media is circulated continuously in the units of the system. The biomass in the system is periodically and/or continuously harvested, represented by stage (D), and directed to a biomass receptacle or it can be fed into a "new system cycle" and/or new units, as represented by the arrow connecting the system cycle to (B). The skilled person will find the optimal timing for the extraction of biomass which mostly depends from the microorganisms metabolic and/or growth rate. The biomass that has been lost from the system at stage (D) can be re-generated by the photosynthetic activity of the microorganisms that remain in the system. This continuous system cycle can optionally be performed in a batch system cycle way, where the liquid media in not continuously circulated in the system but is kept static for a certain period of time (the growth phase), before the biomass is mostly harvested from the system and finally the growth phase is re-initiated by the microorganisms which remain in the system.

FIG. 37 is an illustration of a possible "biofilm driven" cycle of generating and harvesting biomass (either on a continuous or batch basis) using some embodiments of the invention. (A) shows the initial state, when the device is installed and is empty. (B) shows the initiation phase, when the device is filled with liquid media and photosynthetic microorganisms. (C) is the biofilm growth stage. The biofilm begins to develop inside the device. Stage (D) represents biomass generation. The biofilm that has formed is actively photosynthesising and thereby generating more biomass in the liquid media comprised within the device. At stage (E) the biomass has accumulated within the unit of the device and is ready to be harvested. Stage (F) shows biomass being harvested from the device. At this stage, harvested biomass can be directed to a biomass receptacle for collection or it can be fed into a new system cycle, as represented by the arrow connecting (F) to (B). A further cycle can exist between (F), (D) and (E), whereby biomass that has been lost from the system at stage (F) can be re-generated by the photosynthetic activity of the microorganisms that remain in the device. Therefore, (D), (E) and (F) can represent a discrete system within the overall system shown in FIG. 37. Steps (D), (E) and (F) can each occur simultaneously, such that continuous harvesting and continuous regeneration of biomass is achieved using such embodiments of the invention.

The invention is further exemplified by reference to the following non-limiting example.

EXAMPLE

An experimental apparatus was constructed to demonstrate a system according to an embodiment of the present invention. In particular, the apparatus demonstrates that oxygen and carbon dioxide gas transfer occurs through the membrane layers of the photobioreactor unit filled with liquid media and photosynthetic microorganisms.

The case study set-up is represented in a simplified way in FIG. 40.

The unit (201) is made of two polysiloxane membrane layers, 100 microns thick, having a permeability coefficient of oxygen equal to approximately 400 Barrers (at 23° C.+−2° C.), of carbon dioxide equal to approximately 2100 Barrers (at 23° C.+−2° C.) and nitrogen equal to approximately 200 (at 23° C.+−2° C.).

The system (200) is filled with liquid media containing *Synechocystis* sp. culture. The system is air tight, therefore gas exchange between the liquid media in the system and the air outside the system can happen solely through the polysiloxane membrane layers of the unit (201).

Dissolved oxygen concentration levels in the liquid media would be expected to stabilise around the oxygen saturation in water at 30° C.+−2° C. level, which is approximately 7.5 mg/l+−0.3 mg/l.

Introduction of carbon dioxide from the air would expect to result in a pH level drop over time.

The reservoir (202) was been designed to be air tight and to accommodate the sensors (203). The sensors (203) used for this case study were, one optical oxygen sensor "InPro 6860 i" from Mettler Toledo, one pH sensor "601500" from Extech Instruments, one high resolution dual fibre turbidity sensor "InPro 8200" from Mettler Toledo, two temperature immersion probes PT100/Class A, 14132821-TF45 from Wika. Two 36 W fluorescent tubes (205) provided the primary source of illumination. A pressure regulator valve (206) was introduced to regulate the inflation of the unit pressure between the unit (201) and the reservoir (202).

The liquid media temperature was maintained at approximately 30° C. (+−2° C.), the liquid media temperature was maintained by a heated secondary water bath which surrounded the main reservoir (202).

The liquid media was pumped throughout the system intermittently by a peristaltic pump (204) at 730 ml/min. The unit (201) was 19 cm long, 9 cm wide, approximately 1.5 cm thick when fully inflated with liquid media.

Data related to dissolved oxygen concentration level in the liquid media was been recorded in two trial runs (Run A and B). As shown in the graphs illustrated in FIGS. 41a and 41b respectively, oxygen concentration level clearly decreases over the period of the experiments. This indicates that oxygen transmission across the membrane is occurring.

The rate of pH change measured in the medium was partially attenuated by the presence of dissolved compounds (originally contained in the algal medium) that acted as pH buffers. Examples of typical buffer compounds are phosphate salts dissolved in the medium for the provision of essential metabolic nutrients to the culture. Whilst a small decrease in pH was observed during the experimental runs, the magnitude of the pH change that is normally induced by carbon dioxide dissolution in water was neutralized by the action of the buffer. After a significant period of time, beyond the time periods of Run A and B the continuous dissolution of carbon dioxide made the pH change visibly (data not shown).

The results of the experimental runs are presented below.

| RUN A | | |
|---|---|---|
| Type | START | END |
| $O_2$ | 8.69 | 7.69 mg/l (11.50% drop) |
| pH | 10.37 | 10.16 (2.02% drop) |
| Time | 0 | 30 min |

Average temperature 28.4° C. + −2° C.

| RUN B | | |
|---|---|---|
| Type | START | END |
| $O_2$ | 8.63 | 7.31 mg/l (15.29% drop) |
| pH | 10.32 | 10.06 (2.51% drop) |
| Time | 0 | 45 min |

Average temperature 29.5° C. + −2° C.

Although particular embodiments of the invention have been disclosed herein in detail, this has been done by way of example and for the purposes of illustration only. The aforementioned embodiments are not intended to be limiting with respect to the scope of the appended claims, which follow. It is contemplated by the inventors that various substitutions, alterations, and modifications may be made to the invention without departing from the spirit and scope of the invention as defined by the claims.

What is claimed herein is:

1. A method of selective membrane-driven gas transfer, the method comprising:
   providing a liquid to a conduit in a device, wherein the conduit is inflated by liquid media pressure, the device comprising:
      a first membrane layer:
         comprising a flexible polymeric film comprising a polysiloxane elastomer, and having a permeability coefficient through the flexible polymeric film for oxygen not less than 500 Barrer, and for carbon dioxide not less than 1000 Barrer, and
      a second non-membrane layer, at least a portion of which is directly bonded to at least a portion of the first membrane layer to form the conduit; and
   contacting the device with an atmosphere.

2. A selective membrane-driven gas transfer device comprising:
   a first membrane layer comprising a flexible polymeric film comprising a polysiloxane elastomer, and a second non-membrane layer directly bonded to at least a portion of the first membrane layer to form a conduit capable of containing a liquid media and being inflated by liquid media pressure of the liquid media;
   wherein the permeability coefficient through the flexible polymeric film for oxygen is not less than 500 Barrer, and for carbon dioxide is not less than 1000 Barrer.

3. The method of claim 1, wherein the polysiloxane elastomer comprises a polydimethylsiloxane (PDMS) or an elastomer thereof.

4. The method of claim 1, wherein the second non-membrane layer comprises a flexible or inflexible translucent or transparent material.

5. The method of claim 1, wherein the first membrane layer is translucent or transparent.

6. The method of claim 1, wherein the conduit has a length of not less than 5 cm and/or a width of not less than 1 cm.

7. The method of claim 1, wherein the conduit defines an inlet and an outlet to enable fluid to circulate through the device.

8. The method of claim 1, wherein the liquid media flows through the conduit.

9. The method of claim 8, wherein the liquid media flows through the conduit at a fluid velocity of not less than 1 ml/min.

10. The method of claim 1, wherein the first membrane layer and/or the second non-membrane layer comprises an interior-facing surface and an exterior-facing surface, and wherein the interior facing surface is substantially hydrophobic.

11. The method of claim 10, wherein the interior facing surface of the first membrane layer and/or the second non-membrane layer is coated with a hydrophobic coating.

12. The method of claim 11, wherein the hydrophobic coating of the first membrane layer and/or the second non-membrane layer is selected from PTFE, PMMA, PDMS, a fluorosilicone, or a fluorocarbon.

13. The method of claim 11, wherein the interior facing surface of the first membrane layer and/or the second non-membrane layer is machined or physically transformed to be hydrophobic.

14. The method of claim 1, wherein the permeability coefficient through the flexible polymeric film for oxygen is not less than 650, 750, or 820 Barrers.

15. The method of claim 1, wherein the permeability coefficient through the flexible polymeric film for carbon dioxide not less than 2000, 2200, 2500, 2800, 2900, 3000, 3100, 3200, 3300, 3400, 3500, 3600, 3700, 3800, or suitably 3820 Barrers.

16. The method of claim 1, wherein the selective membrane-driven gas transfer occurs between the liquid and the atmosphere outside the device.

* * * * *